(12) United States Patent
Wang et al.

(10) Patent No.: US 7,358,057 B2
(45) Date of Patent: Apr. 15, 2008

(54) QM-7 AND QT-6 CELLS TRANSFECTED WITH MUTANT CELL SURFACE EXPRESSED CHANNEL RECEPTORS AND ASSAYS USING THE TRANSFECTED CELLS

(75) Inventors: Daguang Wang, White Plains, NY (US); Michael De Vivo, New York, NY (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 490 days.

(21) Appl. No.: 10/434,364

(22) Filed: May 9, 2003

(65) Prior Publication Data

US 2004/0009554 A1 Jan. 15, 2004

Related U.S. Application Data

(60) Provisional application No. 60/378,642, filed on May 9, 2002.

(51) Int. Cl.
*C12N 15/09* (2006.01)
*G01N 33/567* (2006.01)

(52) U.S. Cl. .......................... 435/7.2; 435/6; 435/7.21; 435/69.1; 435/349; 436/501

(58) Field of Classification Search ...................... None
See application file for complete search history.

(56) References Cited

U.S. PATENT DOCUMENTS

| | | | |
|---|---|---|---|
| 5,837,489 A | 11/1998 | Elliott et al. | |
| 5,910,582 A | 6/1999 | Elliott et al. | |
| 6,323,000 B2 | 11/2001 | Briggs et al. | |

FOREIGN PATENT DOCUMENTS

| | | |
|---|---|---|
| WO | WO 98/28331 | 7/1998 |
| WO | WO 99/56745 | 11/1999 |
| WO | WO-00/73431 | 12/2000 |

OTHER PUBLICATIONS http://www.atcc.org/common/catalog/numSearch/numResults.cfm?atccNum=CRL-1962, accessed Jun. 28, 2006, product description of cell line QM7 from American Type Culture Collection.*
Kopta et al. Comparison of Mammalian Adult and Fetal Nicotinic Acetylcholine Receptors Stably Expressed in Fibroblasts, Jun. 1994, The Journal of Neuroscience 14(6):3922-3933.*
Bertrand et al., (1993) "Stratification of the channel domain in neurotransmitter receptors" Cell Biology, 5, 688-693.
Bertrand et al., (1993) "Mutations at two distinct sites within the channel domain M2 alter calcium permeability of neuronal $\alpha 7$ nicotinic receptor" Proc. Natl. Acad. Sci., vol. 90, 6971-6975.
Bertrand et al., (1995) "Nicotinic receptor: an allosteric protein specialized for intercellular communication" The Neurosciences, vol. 7, 75-90.
Corringer et al., (2000) "Nicotinic Receptors at the Amino Acid Level" Annu. Rev. Pharmacol. Toxicol, 40, 431-458.
Fucile et al., (2000) "Human neuronal threonine-for-leucine-248 $\alpha 7$ mutant nicotinic acetylcholine receptors are highly $Ca^{2+}$ permeable" PNAS, vol. 97, No. 7, 3643-3648.
Gault et al., (1998) "Genomic Organization and Partial Duplication of the Human $\alpha 7$ Neuronal Nicotinic Acetylcholine Receptor Gene (CHRNA7)" Genomics, 52, 173-185.
Revah et al., (1991) "Mutations in the channel domain alter desensitization of a neuronal nicotinic receptor" Nature, vol. 353, 846-849.
Aylwin et al., "Gating Properties of Mutant Acetylcholine Receptors," Mol. Pharmacology, 46, 1149-1155 (1994).
Bertrand et al., "Unconventional pharmacology of a neuronal nicotinic receptor mutated in the channel domain," Proc. Natl. Acad. Sci., vol. 89, 1261-1265 (1992).
Briggs et al., "Gain of function mutation of the $\alpha 7$ nicotinic receptor: distinct pharmacology of the human $\alpha 7V274T$ variant," Eur. J. Pharmacology, 366, 301-308 (1999).
Fucile et al., "The single-channel properties of human acetylcholine $\alpha 7$ receptors are altered by fusing $\alpha 7$ to the green flourescent protein," PNAS, vol. 99, No. 6, 3956-3961 (2002).
Fucile et al., "Serotonin Antagonizes the Human Neuronal $\alpha 7$ Nicotinic Acetylcholine Receptor and Becomes an Agonist After L248T $\alpha 7$ Mutation," Neuroscience, 110 (1), 169-179 (2002).
Galzi et al., "Mutations in the channel domain of a neuronal nicotinic receptor convert ion selectivity from cationic to anionic," Nature, 359, 500-505 (1992).
Gopalkrishnan et al., "Stable expression and pharmacological properties of the human $\alpha 7$ nicotinic acetylcholine receptor," Eur J Pharmacol, 290, 237-246 (1995).
McIntosh et al., "Conus peptides: novel probes for nicotinic acetylcholine receptor structure and function," Eur. J. Pharmacology, 393, 205-208 (2000).
Palma et al., "Threonine-for-leucine mutation within domain M2 of the neuronal $\alpha 7$ nicotinic receptor converts 5-hydroxytryptamine from antagonist to agonist," Proc. Natl. Acad. Sci. USA, 93, 11231-11235 (1996).

(Continued)

*Primary Examiner*—John Ulm
(74) *Attorney, Agent, or Firm*—Darby & Darby PC; Shelly M. Fujikawa

(57) ABSTRACT

The present invention relates e.g., to QM-7 or QT-6 cells comprising a heterologous mutant nicotinic $\alpha 7$ acetylcholine receptor and/or a nucleic acid encoding it, or a fragment or variant thereof. In a preferred embodiment, the mutant nicotinic $\alpha 7$ acetylcholine receptor subunit has a mutation in the M2 domain. QM-7 and QT-6 cells of the invention are useful for, e.g., assays such as high throughput assays that measure the influx of cations, such as $Ca^{++}$ ions, into a cell. Such assays can be used, e.g., to identify agents that modulate the expression and/or activity of a mutant cell-surface-expressed channel receptor (e.g., the nicotinic $\alpha 7$ receptor), and which thus modulate, e.g., among other functions, processes involved in the central nervous system, such as learning and memory.

35 Claims, 4 Drawing Sheets

OTHER PUBLICATIONS

Sankararamakrishnan et al., "The Pore Domain of the Nicotinic Acetylcholine Receptor: Molecular Modeling, Pore Dimensions, and Electrostatics," *Biophysical Journal*, 71, 1659-1671, (1996).

Seguela et al., "Molecular Cloning, Functional Properties, and Distribution of Rat Brain α7: A Nicotinic Cation Channel Highly Permeable to Calcium," *J. Neuroscience*, 13(2), 596-604 (1993).

Treinin et al., "A Mutated Acetylcholine Receptor Subunit Causes Neuronal Degeneration in *C. elegans*," *Neuron*, 14, 871-877 (1995).

Kassner et al., "Differences in the Fate of Neuronal Acetylcholine Receptor Protein Expressed in Neurons and Stably Transfected Cells," *Journal of Neurobiology*, vol. 33, No. 7, pp. 968-982 (1997).

Hamdan, et al., High-Throughput Screening of G Protein-Coupled Receptor Antagonists Using a Bioluminescence Resonance Energy Transfer 1-Based β-Arrestin2 Recruitment Assay, *J Biomol Screen.*, 2005; 10; 463-75.

Wunder et al., A cell-based cGMP assay useful for ultra-high-throughput screening and identification of modulators of the nitric oxide/cGMP pathway, *Analytical Biochemistry*, 2005, 339: 104-12.

Stauderman, et al., Characterization of Human Recombinant Neuronal Nicotinic Acetylcholine Receptor Subunit Combinations α2β4, α3β4 and α4β4 Stably Expressed in HEK293 Cells, *J Pharmacol Exp Thr.*, 1998, 284 (2):777-789.

Roccamo, et al., Cells defective in sphingolipids biosynthesis express low amounts of muscle nicotinic acetylcholine receptor, *European Journal of Neuroscience*, 1999, 11:1615-1623.

Neff, et al., Production of Polyclonal Antisera that Recognize and Distinguish Between the Extracellular Domains of Neuronal Nicotinic Acetylcholiine Receptor Subunits, *Journal of Neurochemistry*, 1995, 64:332-339.

Atienza, et al., Label-Free and Real-Time Cell-Based Kinase Assay for Screening Selective and Potent Receptor Tyrosine Kinase Inhibitors Using Microelectronic Sensor Array, *J Biomol Screen.*, 2006, 11: 634-643.

\* cited by examiner

QM-7 AND QT-6 CELLS TRANSFECTED WITH MUTANT CELL SURFACE EXPRESSED CHANNEL RECEPTORS AND ASSAYS USING THE TRANSFECTED CELLS

This application claims benefit of U.S. Provisional Application Ser. No. 60/378,642, filed May 9, 2002.

FIELD OF THE INVENTION

The present invention relates e.g., to QM-7 or QT-6 cells comprising a heterologous mutant nicotinic α7 acetylcholine receptor and/or a nucleic acid encoding it, or a fragment or variant thereof. In a preferred embodiment, the mutant nicotinic α7 acetylcholine receptor subunit has a mutation in the M2 domain. QM-7 and QT-6 cells of the invention are useful for, e.g., assays such as high throughput assays that measure the influx of cations, such as $Ca^{++}$ ions, into a cell. Such assays can be used, e.g., to identify agents that modulate the expression and/or activity of a mutant cell-surface-expressed channel receptor (e.g., the nicotinic α7 receptor), and which thus modulate, e.g., among other functions, processes involved in the central nervous system, such as learning and memory.

BACKGROUND OF THE INVENTION

There are two types of receptors for the neurotransmitter, acetylcholine: muscarinic receptors and nicotinic receptors, based on the selectivity of action of muscarine and nicotine, respectively. Muscarinic receptors are G protein-coupled receptors. Nicotinic receptors are members of the ligand-gated ion channel family. When activated, the conductance of ions across the nicotinic ion channels increases. The nicotinic α7 receptor channel is expressed in various brain regions and is believed to be involved in many important biological processes in the central nervous system (CNS), including learning and memory.

Nicotinic α7 receptor protein forms a homo-pentameric channel in vitro that is highly permeable to a variety of cations (e.g., $Ca^{++}$). Each nicotinic α7 receptor protein has four transmembrane domains, named M1, M2, M3 and M4. The M2 domain has been suggested to form the wall lining the channel. Sequence alignment shows that nicotinic α7 receptor protein is highly conserved during evolution. The M2 domain that lines the channel is identical in protein sequence from chicken to human. For discussions of the nicotinic α7 receptor, see, e.g., Revah et al. (1991), *Nature* 353, 846-849; Galzi et al. (1992), *Nature* 359, 500-505; Fucile et al. (2000), *PNAS* 97 (7), 3643-3648; Briggs et al. (1999), *Eur J Pharmacol* 366 (2-3), 301-308; and Gopalakrishnan et al. (1995), *Eur J Pharmacol* 290 (3), 237-246.

Fluorometric imaging is a technique that utilizes the fluorescent signal of $Ca^{++}$-sensitive dyes to detect changes in intracellular $Ca^{++}$. Technology is available to measure cell signals in, e.g., 96 and 384-well formats. One such technology is provided by Molecular Devices Corporation and is called Fluorometric Imaging Plate Reader, or FLIPR. FLIPR allows for high throughput imaging assays, simultaneously detecting $Ca^{++}$ signals from cells, providing real time kinetic data in, e.g., a 96- or 384-well format.

Historically, detection of $Ca^{++}$ signals using nicotinic receptors has been done on isolated cells. Cells transfected with either wild-type or mutant α7 receptor may exhibit changes in $Ca^{++}$ as detected by fluorometric imaging using a fluorescent microscope. In addition, alpha 7 receptors have been screened in a Xenopus oocyte expression system or in stable cell lines (e.g. HEK-293) expressing the α7 receptor, using electrophysiological techniques such as a patch clamp to measure the membrane potential change during depolarization of the channel. Patch-clamp analysis is time consuming and very low throughput. It is not useful for screening compound libraries.

SUMMARY OF THE INVENTION

The present invention is drawn to a QT-6 cell or a QM-7 cell, wherein the cell comprises a heterologous mutant nicotinic α7 acetylcholine receptor or a protein subunit thereof. The invention is further drawn to a QT-6 cell or a QM-7 cell, wherein the cell comprises a heterologous modified mutant nicotinic α7 acetylcholine receptor protein subunit, in which the ligand binding region is substituted with a ligand binding region for one of a 5HT-3, glycine, $GABA_A$, $GABA_C$, or another nicotinic neuronal receptor.

The present invention is drawn to a QT-6 cell or a QM-7 cell, wherein the cell comprises a polynucleotide encoding a heterologous mutant nicotinic α7 acetylcholine receptor protein subunit or a fragment or variant thereof. The invention is further drawn to a QT-6 cell or a QM-7 cell, wherein the cell comprises a polynucleotide encoding a heterologous modified mutant nicotinic α7 acetylcholine receptor protein subunit, wherein the ligand binding region of the receptor protein subunit is substituted with a ligand binding region for one of a 5HT-3, glycine, $GABA_A$, $GABA_C$, or another nicotinic neuronal receptor.

The invention is directed to a method of measuring the activity of a heterologous mutant nicotinic α7 acetylcholine receptor, comprising incubating a QT-6 cell or a QM-7 cell that comprises a heterologous mutant nicotinic α7 acetylcholine receptor in the presence of detectable cations, and detecting the presence of the cations in the cell.

The invention is also directed to a method of identifying an agent which activates a mutant nicotinic α7 acetylcholine receptor, comprising measuring the activity of a QT-6 cell or a QM-7 cell comprising a heterologous mutant nicotinic α7 acetylcholine receptor, exposing the cell to a putative agent and measuring the activity of the receptor in the presence of the agent, and comparing the activity of the receptor in the presence and in the absence of the agent to determine if the agent activates the receptor. The invention is further directed to a method of identifying an agent which inhibits a mutant nicotinic α7 acetylcholine receptor, comprising measuring the activity of a QT-6 or a QM-7 cell comprising a heterologous mutant nicotinic α7 acetylcholine receptor in the presence of an agonist of the receptor, measuring the activity of the receptor in the presence of a putative agent and the agonist, and comparing the activity of the receptor in the presence and in the absence of the agent to determine if the agent inhibits the activation of the receptor.

The invention is drawn to a method of identifying an agent which modulates the expression of a mutant nicotinic α7 acetylcholine receptor, comprising measuring the amount of a heterologous mutant nicotinic α7 acetylcholine receptor in a QT-6 cell or a QM-7 cell, exposing the cell to a putative agent and measuring the amount of the receptor in the presence of the agent, and comparing the amount of the receptor in the presence and in the absence of the agent to determine if the agent modulates the expression of the receptor.

The invention is drawn to a method of making a QT-6 cell or a QM-7 cell, wherein the cell comprises a heterologous mutant nicotinic α7 acetylcholine receptor or a protein subunit thereof, comprising introducing a construct comprising a nucleic acid encoding a mutant nicotinic α7 acetylcholine receptor protein subunit to a QT-6 cell or a QM-7 cell. The invention is further drawn to a method of producing a mutant nicotinic α7 acetylcholine receptor protein subunit, comprising introducing a construct comprising a nucleic acid encoding a mutant nicotinic α7 acetylcholine receptor protein subunit to a QT-6 cell or a QM-7 cell, culturing the cell under conditions effective to express the protein subunit, and recovering the protein subunit.

The invention is also directed to a kit comprising a QT-6 cell or a QM-7 cell, wherein the cell comprises a heterologous mutant nicotinic α7 acetylcholine receptor or a protein subunit thereof, and a $Ca^{++}$ sensitive dye.

DESCRIPTION OF THE INVENTION

The present invention relates e.g., to a QT-6 cell or a QM-7 cell (the QT-6 cell line is the parent line from which the QM-7 cell line was derived) that comprises a heterologous cell-surface expressed channel receptor or subunit thereof.

Both QT-6 and QM-7 cells are readily available, e.g., from the ATCC, as ATCC numbers CRL-1708 and CRL-1962, respectively. In general, the discussion herein refers to QM-7 cells, which are preferred. However, it will be clear to the skilled worker that the invention applies equally well to QT-6 cells.

The invention relates to QT-6 or QM-7 cells comprising any mutant nicotinic α7 acetylcholine receptor or a protein subunit thereof. Such cells will provide, e.g., assays of superior quality, e.g., sensitivity etc. as discussed below, in comparison to analogous assays performed with other conventional cells, e.g., CHO or HEK-293 cells. In a preferred embodiment, the cell-surface expressed channel receptor subunit is a mutant α7 nicotinic acetylcholine receptor (nAChR) subunit (polypeptide) having a mutation in the M2 domain, wherein, among other things, said mutation results in slower desensitization than does the wild type α7 polypeptide, thereby allowing stronger and longer-lasting $Ca^{++}$ influx into the cell than does the wild type α7 polypeptide, further enhancing assay superiority, as further discussed below. Examples of such mutations include, e.g., for the human polypeptide, Leu at position 270 substituted with a Thr (L270T), and Val at position 274 substituted with a Thr (V274T). In general, much of the discussion herein refers to nicotinic α7 polypeptides, particularly mutant nicotinic α7 polypeptides. However, it will be clear to the skilled worker that the invention also applies to other cell-surface expressed channel receptors and/or receptor subunits that incorporate portions of the mutant nicotinic α7 receptor.

The invention is drawn to a QT-6 cell or a QM-7 cell, wherein the cell comprises a heterologous mutant nicotinic α7 acetylcholine receptor or a protein subunit thereof. In a preferred embodiment, the receptor is a mammalian receptor, preferably a human, monkey, or rat receptor. In a further preferred embodiment, the receptor or the protein subunit has a mutation in the M2 domain. It is preferred that the receptor or the protein subunit is human, monkey, or rat and the Leu at position 270 is substituted with Thr or the Val at position 274 is substituted with a Thr. Preferably, the cell of the invention is a QM-7 cell.

The invention also relates to a QT-6 or QM-7 cell comprising a polynucleotide encoding a cell-surface expressed channel receptor polypeptide (e.g., a mutant α7 receptor as mentioned above), or comprising a fragment or variant of the polynucleotide or polypeptide.

The invention is drawn to a QT-6 cell or a QM-7 cell, wherein the cell comprises a polynucleotide encoding a heterologous mutant nicotinic α7 acetylcholine receptor protein subunit or a fragment or variant thereof. In a preferred embodiment, the receptor is a mammalian receptor, preferably a human, monkey, or rat receptor. In a further preferred embodiment, the receptor or the protein subunit has a mutation in the M2 domain. It is preferred that the receptor or the protein subunit is human, monkey, or rat and the Leu at position 270 is substituted with Thr or the Val at position 274 is substituted with a Thr. Preferably, the cell of the invention is a QM-7 cell.

In general, the cell-surface expressed channel receptor or receptor subunit (e.g. mutant α7) polynucleotides or polypeptides of the invention are heterologous to the QM-7 or QT-6 cells.

The invention also relates to assays using QT-6 or QM-7 cells of the invention to measure the uptake of cations, such as, e.g., $Ca^{++}$, $Rb^{+}$, $Na^{+}$, $K^{+}$, $Ba^{++}$, or other cations, preferably $Ca^{++}$ ions, into the cell (e.g., real time, high throughput, imaging assays, using, e.g., FLIPR), and to methods for identifying agents which interact with, or regulate expression or activity of, cell-surface expressed channel receptors and/or subunits thereof (e.g., α7 polypeptides and/or receptors that comprise α7 polypeptides), using such assays.

An advantage of the QT-6 or QM-7 cells of the invention is that they exhibit more efficient functional expression of membrane-bound receptor proteins, e.g., channel receptors, than do other cells (such as, e.g., HEK-293 cells or CHO cells). Without wishing to be bound to any particular mechanism, it is proposed that the higher functional expression is a result of, e.g., more efficient transport of the protein to the membrane, better positioning of the receptor protein in the membrane, or the like. This allows for higher sensitivity, stability, reproducibility and/or reliability in assays for activities of such receptors than with other cell types. Moreover, in the case of QM-7 cells comprising mutant α7 polypeptides as discussed above, the cells exhibit stronger and longer-lasting influx of ions, such as $Ca^{++}$ ions, than do other cells (such as, e.g., HEK-293 cells or CHO cells) that comprise such a mutant α7. In addition, the QM-7 and QT-6 cells of the invention when stably transfected do not lose activity with repeated passage as compared to other cells transfected with mutant receptors described herein. Thus, QM-7 cells of the invention are particularly advantageous for use in, e.g., real time, high throughput, $Ca^{++}$ imaging assays, using, e.g., FLIPR. Example IVb and FIG. 2 illustrate the superiority of QM-7 cells comprising a mutant α7 of the invention compared to HEK-293 cells comprising the mutant α7, in such an assay.

The invention is directed to a method of measuring the activity of a heterologous mutant nicotinic α7 acetylcholine receptor, comprising incubating a QT-6 cell or a QM-7 cell that comprises a heterologous mutant nicotinic α7 acetylcholine receptor in the presence of detectable cations, and detecting the presence of the cations in the cell. In a preferred embodiment, the detectable cations are one of $Ca^{++}$, $Rb^{+}$, $Na^{+}$, $K^{+}$, or $Ba^{++}$, preferably the detectable cations are $Ca^{++}$. In a preferred embodiment, the cell is a QM-7 cell.

The invention is further directed to a method of identifying an agent which activates a mutant nicotinic α7 acetylcholine receptor, comprising measuring the activity of a QT-6 cell or a QM-7 cell comprising a heterologous mutant nicotinic α7 acetylcholine receptor, exposing the cell to a putative agent and measuring the activity of the receptor, in the presence of the agent, and comparing the activity of the receptor in the presence and in the absence of the agent to determine if the agent activates the receptor. In one embodiment, the agent modulates ion transport through a channel or regulates an allosteric site of the receptor. In a preferred embodiment, the activity of the receptor is determined by measuring the amount of detectable cation influx into the cell. Preferably, the detectable cation is one of $Ca^{++}$, $Rb^+$, $Na^+$, $K^+$, or $Ba^{++}$, more preferably, the detectable cation is $Ca^{++}$.

The invention is directed to a method of identifying an agent which inhibits a mutant nicotinic α7 acetylcholine receptor, comprising measuring the activity of a QT-6 or a QM-7 cell comprising a heterologous mutant nicotinic α7 acetylcholine receptor in the presence of an agonist of the receptor, measuring the activity of the receptor in the presence of a putative agent and the agonist, and comparing the activity of the receptor in the presence and in the absence of the agent to determine if the agent inhibits the activation of the receptor. In one embodiment, the agent modulates ion transport through a channel or regulates an allosteric site of the receptor. In a preferred embodiment, the activity of the receptor is determined by measuring the amount of detectable cation influx into the cell. In a preferred embodiment, the detectable cation is one of $Ca^{++}$, $Rb^+$, $Na^+$, $K^+$, or $Ba^{++}$, more preferably, the detectable cation is $Ca^{++}$.

The invention is also drawn to a method of identifying an agent which modulates the expression of a mutant nicotinic α7 acetylcholine receptor, comprising measuring the amount of a heterologous mutant nicotinic α7 acetylcholine receptor in a QT-6 cell or a QM-7 cell, exposing the cell to a putative agent and measuring the amount of the receptor in the presence of the agent, and comparing the amount of the receptor in the presence and in the absence of the agent to determine if the agent modulates the expression of the receptor. In one embodiment, the agent modulates the transport of a subunit of the mutant nicotinic α7 acetylcholine receptor to the cell surface membrane.

In the above methods, the receptor is preferably a mammalian receptor, more preferably a human, monkey, or rat receptor. In a preferred embodiment, the receptor has a mutation in the M2 domain. In a further preferred embodiment, the receptor is human, monkey, or rat and the Leu at position 270 is substituted with Thr or the Val at position 274 is substituted with a Thr.

Other aspects of the invention include a QM-7 cell of the invention which is transiently transfected with a mutant α7 polynucleotide that comprises a mutation in its M2 domain, and which expresses said mutant polypeptide transiently; or which is stably transfected with such a mutant α7 polynucleotide, and which expresses said mutant polypeptide stably; wherein the mutant α7 polypeptide is human; wherein the mutation in the human α7 polypeptide is L270T or V274T, or is equivalent to the chick α7 mutation L247T, L247S, L247F, L247V, V251T, T244Q, E237A/V251T, E237A/L247T, E237A/L247S, E237A/L247V, E237A/L247F, E237A/T244Q, L237A/L254T, or 237/L255T; wherein the mutation in the α7 polypeptide is L270T; wherein the mutant α7 polypeptide is chicken; or wherein the mutation in the chicken α7 polypeptide is L247T, L247S, L247F, L247V, V251T, T244Q, E237A/V251T, E237A/L247T, E237A/L247S, E237A/L247V, E237A/L247F, E237A/T244Q, E237A/L254T, or E237A/L255T.

Further aspects of the invention include a method to measure the activity of a surface-expressed channel receptor polypeptide or a receptor comprising at least one such polypeptide (e.g., a mutant α7 polypeptide as above, or a receptor comprising at least one such mutant α7 subunit), comprising incubating a QM-7 cell of the invention in the presence of detectable cations, and detecting the presence of said cations in the cell; wherein said cations are $Ca^{++}$, $Rb^+$, $Na^+$, $K^+$ or $Ba^{++}$ ions, particularly $Ca^{++}$ ions; wherein the assay is a high throughput assay, e.g. wherein the method is a real time, high throughput, Ca imaging assay, using FLIPR.

The invention is further relates to a method of identifying an agent which modulates the activity of a surface-expressed channel receptor polypeptide or a receptor comprising at least one such polypeptide (e.g., an α7 polypeptide or a receptor comprising at least one α7 subunit), comprising exposing a QM-7 cell of the invention to a putative agent, e.g., in the presence of a ligand that stimulates the receptor, and measuring the activity of the polypeptide or receptor; wherein the agent is an agonist of the receptor; wherein the agent is an antagonist of the receptor; wherein the agent modulates ion transport through the channel; or wherein the agent regulates the allosteric site of the receptor.

The invention also is directed to a method of making a QT-6 cell or a QM-7 cell, wherein the cell comprises a heterologous mutant nicotinic α7 acetylcholine receptor or a protein subunit thereof, comprising introducing a construct comprising a nucleic acid encoding a mutant nicotinic α7 acetylcholine receptor protein subunit to a QT-6 cell or a QM-7 cell. In one embodiment, the cell is stably transfected. The invention is further directed to a method of producing a mutant nicotinic α7 acetylcholine receptor protein subunit, comprising introducing a construct comprising a nucleic acid encoding a mutant nicotinic α7 acetylcholine receptor protein subunit to a QT-6 cell or a QM-7 cell, culturing the cell under conditions effective to express the protein subunit, and recovering the protein subunit.

The invention also relates to a kit comprising a QT-6 cell or a QM-7 cell, wherein the cell comprises a heterologous mutant nicotinic α7 acetylcholine receptor or a protein subunit thereof, and a $Ca^{++}$ sensitive dye.

The invention is additionally drawn to QT-6 or QM-7 cells, wherein the cells comprise a variety of chimeric constructs of the recognition site of a heterologous cell-surface expressed channel receptor protein and the calcium conduction site of the nicotinic α7 acetylcholine receptor protein, or nucleic acids encoding such chimeric protein constructs. Non-limiting examples of cell-surface expressed channel receptors include ligand-gated receptors such as, e.g., receptors for 5HT-3, glycine, $GABA_A$, $GABA_C$, or nicotinic α3, or α4 neuronal receptors.

The invention is drawn to a QT-6 cell or a QM-7 cell, wherein the cell comprises a heterologous modified mutant nicotinic α7 acetylcholine receptor protein subunit, in which the ligand binding region is substituted with a ligand binding region for one of a 5HT-3, glycine, $GABA_A$, $GABA_C$, or another nicotinic neuronal receptor, preferably a nicotinic α3 or α4 neuronal receptor. The invention is further drawn to a QT-6 cell or a QM-7 cell, wherein the cell comprises a polynucleotide encoding a heterologous modified mutant nicotinic α7 acetylcholine receptor protein subunit, wherein the ligand binding region of the receptor protein subunit is substituted with a ligand binding region for one of a 5HT-3, glycine, $GABA_A$, $GABA_C$, or another nicotinic neuronal receptor, preferably a nicotinic α3 or α4 neuronal receptor.

In a preferred embodiment, the QM-7 cells comprise an α7 subunit (polypeptide) alpha 7 polypeptides of the invention may originate from any of a variety of species, e.g., human, rat, mouse, monkey, bovine, chicken, and C.

*elegans*, preferably human. An α7 subunit is a subunit of an nAChR to which ACh binds. In general, α7 subunits exhibit conservation of adjacent Cys residues in the extracellular domain of the subunit that are the homologues of cysteines 192 and 193 of the Torpedo alpha subunit (see Noda et al. (1982) *Nature* 299, 793-797). In general, α7 subunits are encoded by nucleic acids that hybridize under conditions of high stringency to at least one of the α7 mutant-encoding nucleic acids described herein, e.g., SEQ ID NO: 3. Splice variants of α7 are also encompassed by the invention.

The M2 domains (generally about 20 amino acids in length) of α7 polypeptides have been characterized from a variety of species and shown to play an important role in ion permeation through nAChR channels. See, e.g., Changeux et al. (1992) *Q. Rev. Biophys* 25, 395-432; Bertrand et al. (1993) *Proc. Natl. Acad. Sci* 90, 6971-6975; and Revah et al., (1991) *Nature* 353, 846-849. At least the following mutations of M2 domains have been shown to lead to slower desensitization than the wild type protein: in the human protein: L270T and V274T; in the chicken protein: L247T; L247S; L247F; L247V; V25IT; T244Q; and the double mutant E237A/V251T. Mutations of the human 270 and 274 residues (and comparable residues in the protein from other species) to other polar residues also give rise to the desired phenotype. Double mutants, such as the chicken E237A plus, e.g., V251T, L247T, L247S, L247V, L247F, T244Q, L254T or L255T are also encompassed by the invention. Other residues, when mutated, also lead to slower desensitization, e.g., residues which face the channel lumen and are aligned along the meridian of an a-helix. See, e.g., Bertrand et al. (1995) *The Neurosciences* 7, 75-90 and Bertrand et al. (1993), *Current Opinion in Cell Biology* 5, 688-693.

Thus, the invention relates to QM-7 cells comprising any α7 mutant in which a mutation in the M2 domain gives rise to the phenotype of slower desensitization, including the human mutant α7's L270T and V274T; the chicken mutants L247T, L247S, L247F, L247V, V251 T, T244Q, and the double mutants E237A/V251 T, E237A/L247T, E237A/L247S, E237A/L247V, E237A/L247F, E237A/T244Q, L237A/L254T, or E237A/L255T; and other mutants as discussed above. Of course, mutations in the human α7 protein (or α7 proteins from other species) in residues which are comparable to mutated residues in the chicken α7 protein, such as those discussed above, are also encompassed by the invention.

In a preferred embodiment, a QM-7 cell of the invention comprises a human α7 polypeptide (and/or nucleic acid encoding it) having an L270T mutation.

Methods to generate any of the mutants discussed herein are conventional and well known in the art. For example, various methods of site-specific mutagenesis are known. Procedures for this and other molecular biology techniques discussed herein are found in many readily available sources, e.g., Sambrook, et al., Molecular Cloning: A Laboratory Manual, Second Edition, Cold Spring Harbor, N.Y., (1989); Wu et al, *Methods in Gene Biotechnology* (CRC Press, New York, N.Y., 1997); *Recombinant Gene Expression Protocols, in Methods in Molecular Biology*, Vol. 62, (Tuan, ed., Humana Press, Totowa, N.J., 1997); and Current Protocols in Molecular Biology, (Ausabel et al, Eds.,), John Wiley & Sons, NY (1994-1999), among many others. See also methods in U.S. Pat. No. 6,323,000, and Examples I-III herein, which illustrates a method to generate human, monkey, and rat α7 L270T.

A QM-7 cell of the invention may contain a functional fragment or variant of a receptor subunit. For example, it may contain a fragment or variant of a mutant α7 polypeptide (i.e., a fragment or variant that retains a mutation in the M2 domain). The terms "functional fragment" or "functional variant" in this context mean a polypeptide that retains substantially the properties of the mutant α7 polypeptide, i.e., exhibits slower desensitization than does the wild type α7 polypeptide, thereby allowing stronger and longer-lasting $Ca^{++}$ influx into the cell than does the wild type α7 polypeptide.

Functional fragments may be of any length that is compatible with the invention, i.e., a long enough length to retain the functional region of the protein. For example, a QM-7 cell comprising a functional fragment of a mutant α7 polypeptide as above retains the ability to allow ligand-stimulated influx of, e.g., $Ca^{++}$ ions into the cell, and to exhibit slower densensitization than wild type α7. For example, the protein may lack part or all of the C-terminal, extracellular amino acids encoded by exon 10, or may lack one or more N-terminal amino acids encoded by exon 1.

Functional variants may be of any type that is compatible with the invention. For example, functional variants of a mutant α7 (i.e., which retain a mutation as above in the α7 M2 domain) include polypeptides that contain mutations in regions of the protein that are non-essential for the purposes of the invention (e.g., for use in assays of $Ca^{++}$ influx into the cell), wherein the additional mutations do not interfere with the ability of the protein to function for purposes of the invention. Such non-essential regions include, e.g., the intracellular loop encoded by exons 9 and 10; and the extracellular segment encoded by exon 10. One or more mutations can occur in each such non-essential region, and one or more of the non-essential regions can be mutated.

The mutations in these non-essential regions include, e.g., muteins, analogs and derivatives. A variant polypeptide can differ in amino acid sequence by, e.g., one or more additions, substitutions (either with conservative or non-conservative amino acids), deletions (partial or complete deletions of a non-essential segment), insertions, inversions, fusions, and truncations, or a combination of any of these.

Part or all of deletions in the non-essential regions may, optionally, be replaced by other, non-naturally occurring or heterologous, amino acid sequences, provided that the replacement sequences do not substantially interfere with the activity of the α7, i.e., do not inhibit the influx of cations, such as $Ca^{++}$ ions, into cells comprising the α7. Examples of such replacement sequences include, e.g., targeting sequences, peptides having an enzymatic function or providing antibiotic resistance, or other functional or diagnostic peptides. Alternatively, the replacement sequence may allow for identification and/or purification of a mutant α7 polypeptide of the present invention e.g., a hexa-histidine tag (e.g., as supplied by a pQE-9 vector) or a hemagglutinin (HA) tag. The HA tag corresponds to an epitope derived from the influenza hemagglutinin protein (Wilson, I., et al., Cell, 37:767 (1984)). Many other such replacement sequences will be evident to one of skill in the art.

Another type of variant encompassed by the invention is one in which the leader sequence (e.g., the leader sequence encoded by exon 1 of α7) is replaced by part of all of a leader sequence from a secreted or membrane bound protein, from any of a variety of other organisms, e.g., leader sequences from a variety of growth factors such as, e.g., NGF, GCSF, or PDGF; or from any of a variety of other ligand-gated receptor polypeptides or G-coupled receptor polypeptides; or from any of a variety of other cell-surface-expressed receptors. Many such leader sequences are known, and can be used, provided that they allow the polypeptide (e.g., the α7 polypeptide) to become located properly in the cell membrane. Methods of testing whether such mutants allow proper positioning of the α7 polypeptide are conventional.

Mutations may also occur in the essential regions of the polypeptide, provided that they do not alter its function with respect to the purpose of the invention (e.g., allowing ligand-stimulated influx of, e.g., $Ca^{++}$ ions). Such mutations include, e.g., insertions, deletions or substitutions. For example, conservative amino acid substitutions, which are well known to those of skill in the art, generally do not lead to a change in protein function. Typical conservative substitutions, which preserve the general charge, hydrophobicity/hydrophilicity, side chain moiety and/or stearic bulk of the amino acid substituted, include, e.g., Gly/Ala. Va/Ile/Leu, Asp/Glu, Lys/Arg, Asn/Gln, Thr/Ser and Phe/Trp/Tyr.

Also included in the invention are variant polypeptides that have varying degrees of sequence homology (identity) to a cell-surface expressed channel receptor subunit, e.g., to an α7 polypeptide which comprises a mutation as noted above in its M2 domain. That is, the variant polypeptides are substantially homologous to said polypeptide, or show substantial sequence homology (sequence identity) thereto. Thus, polypeptides and fragments thereof within the present invention may contain amino acid sequences which show at least about 65% sequence homology (identity) to the polypeptides of the invention, preferably about 70-75% or 80-85% sequence homology (identity) thereto, and most preferably about 90-95% or 97-99% sequence homology (identity) thereto. The invention also encompasses polypeptides having a lower degree of sequence identity, but having sufficient similarity so as to perform the desired activity of the α7 protein.

In one embodiment, the amino acid sequences which exhibit less than 100% identity to said polypeptide lie within non-essential regions; in another embodiment, they lie within essential regions; and in another embodiment, they lie within both essential and non-essential regions.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100 [1−(C/R)]

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences of α7, having about 502 amino acid residues, at least 150, preferably at least 200, more preferably at least 250, even more preferably at least 300, and even more preferably at least 350, 400, 450 or 475 amino acid residues are aligned).

The description herein for percent identity or percent homology is intended to apply equally to nucleotide or amino acid sequences The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

A preferred, non-limiting example of such a mathematical algorithm is described in Karlin et al. (1993) Proc. Natl. Acad. Sci. USA 90:5873-5877. Such an algorithm is incorporated into the NBLAST and XBLAST programs (version 2.0) as described in Altschul et al. (1997) Nucleic Acids Res. 25:3389-3402. When utilizing BLAST and Gapped BLAST programs, the default parameters of the respective programs (e.g., NBLASST) can be used. In one embodiment, parameters for sequence comparison can be set at score=100, wordlength-12, or can be varied (e.g., W=5 or W=20).

In a preferred embodiment, the percent identity between two amino acid sequences is determined using the Needleman et al. (1970) (J. Mol. Biol. 48:444-453) algorithm which has been incorporated into the GAP program in the GCG software package using either a BLOSUM 62 matrix or a PAM250 matrix, and a gap weight of 16, 14, 12, 10, 8, 6, or 4 and a length weight of 1, 2, 3, 4, 5 or 6. In yet another preferred embodiment, the percent identity between two nucleotide sequences is determined using the GAP program I the GCG software package (Devereux et al. (1984) Nucleic Acids Res. 12 (1):387) using a NWSgapdna. CMP matrix and a gap weight of 40, 50, 60, 70, or 80 and a length weight of 1, 2, 3, 4, 5 or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) Comput. Appl. Biosci. 10:3-5; and FASTA described in Pearson et al. (1988) PNAS 85:2444-8.

In accordance with the present invention, the term "substantially homologous," when referring to a protein sequence, means that the amino acid sequences are at least about 90-95% or 97-99% or more identical. A substantially homologous amino acid sequence can be encoded by a nucleic acid sequence hybridizing to the nucleic acid sequence, or portion thereof, of a sequence encoding a mutant polypeptide of the invention, under conditions of high stringency.

Conditions of "high stringency," as used herein, means, for example, incubating a blot is overnight (e.g., at least 12 hours) with a long polynucleotide probe in a hybridization solution containing, e.g., about 5×SSC, 0.5% SDS, 100 µg/ml denatured salmon sperm DNA and 50% formamide, at 42° C. Blots can be washed at high stringency conditions that allow, e.g., for less than 5% bp mismatch (e.g., wash twice in 0.1×SSC and 0.1% SDS for 30 min at 65° C.), thereby selecting sequences having, e.g., 95% or greater sequence identity.

Other non-limiting examples of high stringency conditions include a final wash at 65° C. in aqueous buffer containing 30 mM NaCl and 0.5% SDS. Another example of high stringent conditions is hybridization in 7% SDS, 0.5 M $NaPO_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

In another aspect of the invention, the mutant α7 receptor polypeptide is modified to generate a chimeric receptor, in which the ligand binding region is substituted by another ligand binding region such as, e.g., one for 5HT-3, glycine, $GABA_A$, $GABA_C$ or other neuronal nicotinic receptors, such as, e.g., α3 or α4. QM-7 cells comprising such chimeric α7 receptor polypeptides exhibit a slow desensitization phenotype that allows stronger and longer-lasting ion influx, e.g., $Ca^{++}$ influx, through the channel than do QM-7 cells, or other cells, that comprise wild type ligand-gated channels for 5HT-3, glycine, $GABA_A$ or $GABA_C$, or other neuronal nicotinic receptors. By subjecting such cells to assays such as those described herein, e.g., real time, high throughput, imaging assays (of, e.g., $Ca^{++}$), using FLIPR, one can identify agents that modulate the ligand binding activity of the receptor moieties noted above. Alternatively, using such cells, one can identify agents that modulate other activities of the receptor (e.g., activities of the channel, itself), by stimulating the cells with agents that act on those ligands, and measuring the ion (e.g., $Ca^{++}$) influx into the cell, e.g., serotonin for the 5HT-3 receptor.

QM-7 cells comprise a variety of endogenous subunits which can form heteromeric receptors that include one or more heterologous cell-surface expressed channel receptor subunits, e.g., endogenous subunits in combination with heterologous α7 subunits. Such endogenous subunits include, e.g., α1, α2α, β and γ, and other subunits present at neuromuscular junctions. Although the combination of nAChR subunits with subunits related to other types of receptors (e.g., other classes of ligand-gated ion channel) has not been demonstrated, it is within the scope of the present invention that such combinations are possible. Thus, the invention encompasses, e.g., both homooligomeric nAChRs in which the only subunit is a mutant α7 and heteromeric nAChRs comprising at least one mutant α7. In this context, the term "a variant" (nAChR) receptor means a receptor that comprises at least one mutant α7 subunit.

The invention also includes QM-7 cells comprising (e.g., transfected by) nucleic acids, e.g., cDNA or genomic DNA, encoding cell surface expressed channel receptor subunits, e.g., α7 polypeptides that contain one or more mutations as above in the M2 domain, and functional fragments or variants thereof. The invention also includes QM-7 cells comprising polynucleotides that code without interruption for such receptor subunits. A polynucleotide that "codes without interruption" refers to a polynucleotide having a continuous open reading frame ("ORF") as compared to an ORF which is interrupted by introns or other noncoding sequences.

Such a polynucleotide may be a recombinant polynucleotide, a natural polynucleotide (e.g., naturally containing a mutation), or a synthetic or semi-synthetic polynucleotide, or combinations thereof. As used herein, the terms polynucleotide and nucleic acid are interchangeable.

As used herein, the term "gene" means a segment of DNA involved in producing a polypeptide chain; it may include regions preceding and following the coding region (leader and trailer) as well as intervening sequences (introns) between individual coding segments (exons). Of course, cDNAs lack the corresponding introns. The invention includes QM-7 cells comprising partial or complete genes (e.g., genomic clones) that encode polypeptides of the invention. Genomic clones of α7 genes are reported, e.g., in Gault et al. (1998), *Genomics* 52, 173-185 (human), and Matter-Sadzinski et al. (1992), *EMBO J* 11, 4529-4538 (chick).

Methods of making the QM-7 cells of the invention are conventional. In general, one introduces (e.g., transfects) a nucleic acid encoding a cell surface expressed channel receptor (e.g., a mutant α7 polypeptide) into a QM-7 cell, using art-recognized procedures. Methods of generating a nucleic acid that encodes such a cell surface expressed channel receptor (e.g., mutant α7) are conventional and are discussed elsewhere herein.

Any nucleic acid that encodes a polypeptide of the invention, including functional variants or fragments as discussed elsewhere herein, can be used to generate a QM-7 cell of the invention. For example, a coding sequence may be identical to the coding sequence for a mutant α7, or it may be a different coding sequence, which, as a result of the redundancy or degeneracy of the genetic code, encodes the same polypeptide as the mutant α7 coding sequence. Such a nucleic acid is sometimes referred to herein as a "degenerate variant." Allelic variants are also encompassed by the invention. That is, a polynucleotide may have a coding sequence that is a naturally or non-naturally occurring allelic variant of a coding sequence used to generate the mutant α7-containing nucleic acid As is known in the art, an allelic variant is an alternate form of a polynucleotide sequence that may have a substitution, deletion or addition of one or more nucleotides, which in general does not substantially alter the function of the encoded polypeptide.

Polynucleotides encoding the cell surface expressed channel receptor subunits (e.g., mutant α7 polypeptides) may have a conventional sugar-phosphate backbone, or the nucleotides may be joined via various known linkages, e.g., ester, sulfamate, sulfamide, phosphorothioate, phosphoramidate, methylphosphonate, carbamate, etc., depending on the desired purpose, e.g., resistance to nucleases, such as RNAse H, improved in vivo stability, etc. See, e.g., U.S. Pat. No. 5,378,825. The polynucleotides may also comprise nucleotide or nucleoside analogs, such as e.g., inosine, thionucleotides, 6-mercaptoguanine, 8-oxo-guanine, or the like.

In general, the QM-7 cells are transfected with recombinant constructs that contain expression vectors plus the polynucleotides as discussed above. The expression vector can be, e.g., a plasmid or viral vector, into which a polynucleotide sequence of the invention has been inserted, so as to be operatively linked to an appropriate expression control (regulatory) sequence(s) (e.g., promoters and/or enhancers)

which directs mRNA synthesis. Appropriate expression control sequences, e.g., regulatable promoter or regulatory sequences known to control expression of genes in eukaryotic cells or their viruses, can be selected for expression in the QM-7 cells. Preferred expression control sequences are derived from highly-expressed genes, e.g., from operons encoding glycolytic enzymes such as 3-phosphoglycerate kinase (PGK), α-factor, acid phosphatase, or heat shock proteins, among others. Such expression control sequences can be selected from any desired gene, e.g using CAT (chloramphenicol transferase) vectors or other vectors with selectable markers. Two appropriate vectors for such selection are pKK232-8 and pCM7.

Appropriate promoters include CMV immediate early, HSV thymidine kinase, early and late SV40, adenovirus promoters, LTRs from retrovirus, and mouse metallothionein-I. Selection of an appropriate promoter is well within the level of ordinary skill in the art.

Transcription of the DNA encoding the polypeptides of the present invention can be increased by inserting an enhancer sequence into the expression vector. Enhancers are cis-acting elements of DNA, usually about from 10 to 300 bp that act on a promoter to increase its transcription. Representative examples include the SV40 enhancer on the late side of the replication origin bp 100 to 270, a cytomegalovirus early promoter enhancer, the polyoma enhancer on the late side of the replication origin, and adenovirus enhancers.

In one embodiment of the invention, the mutant α7 coding sequences are placed under the control of the natural regulatory sequences (e.g., promoter and/or enhancer elements) of the α7 gene. A genomic clone of the human α7 gene has been reported. Methods for obtaining the regulatory elements from such a genomic clone and placing a cDNA encoding a mutant α7 of the invention under their control are conventional. In another embodiment, the genomic clone, itself, is placed into an appropriate vector and then transfected into a QM-7 cell; and/or sequences from the genomic clone, including one or more introns, optionally plus cDNA sequences, are engineered into an appropriate expression vector and transfected into a QM-7 cell.

Generally, recombinant expression vectors also include origins of replication. An expression vector may contain a ribosome binding site for translation initiation, a transcription termination sequence, a polyadenylation site, splice donor and acceptor sites, and/or 5' flanking or non-transcribed sequences. DNA sequences derived from the SV40 splice and polyadenylation sites may be used to provide required nontranscribed genetic elements. The vector may also include appropriate sequences for amplifying expression. In addition, expression vectors preferably contain one or more selectable marker genes to provide a phenotypic trait for selection of transformed host cells, such as dihydrofolate reductase or neomycin resistance.

Large numbers of suitable expression vectors are known to those of skill in the art, and many are commercially available. Suitable vectors include chromosomal, nonchromosomal and synthetic DNA sequences, e.g., derivatives of SV40; phage DNA; baculovirus; yeast plasmids; vectors derived from combinations of plasmids and viral DNA such as vaccinia, adenovirus, adeno-associated virus, TMV, fowl pox virus, and pseudorabies. However, any other vector may be used as long as it is replicable and viable in a host. Appropriate cloning and expression vectors are described, e.g., by Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), *Recombinant Gene Expression Protocols, in Methods in Molecular Biology*, Vol. 62, (Tuan, ed., Humana Press, Totowa, N.J., 1997), and *Current Protocols in Molecular Biology*, (Ausubel et al, Eds.,), John Wiley & Sons, NY (1994-1999).

Appropriate DNA sequences may be inserted into a vector by any of a variety of procedures. In general, the DNA sequence is inserted into an appropriate restriction endonuclease site(s) by procedures known in the art. Such procedures and others are deemed to be within the scope of those skilled in the art. Conventional procedures are found in many readily available sources, e.g., Sambrook, et al., Molecular Cloning: A Laboratory Manual, Second Edition, Cold Spring Harbor, N.Y., (1989). See also Graham et al. (1988) *Virology* 63 614-617 for a rescue recombination technique useful for the construction of, e.g., adenoviral gene delivery vehicle.

The present invention also relates to QM-7 cells that are transfected with constructs such as those described above, and to progeny of said cells, especially where such cells result in a stable cell line that can be used for assays of $Ca^{++}$ uptake, e.g., in order to identify agents which modulate α7 activity or expression, and/or for production (e.g., preparative production of membrane-associated protein) of the mutant α7 polypeptides of the invention. The exogenous polynucleotide that is transfected into a QM-7 cell may be directly transcribed and translated by the cell, maintained as a nonintegrated vector (e.g., as a plasmid), or, alternatively, may be stably integrated into the host genome.

Introduction of a construct into a host cell can be effected by, e.g., calcium phosphate transfection, DEAE-Dextran mediated transfection, lipofection, a gene gun, or electroporation (See, e.g., Davis, L., Dibner, M., Battey, I., Basic Methods in Molecular Biology, (1986)).

Following transfection of QM-7 and growth to an appropriate cell density, the promoter can be induced by appropriate means (e.g., temperature shift or chemical induction), if desired, and cells cultured for an additional period. The engineered host cells are cultured in conventional nutrient media modified as appropriate for activating promoters (if desired), selecting transformants, amplifying the mutant genes of the present invention, or performing assays. The culture conditions, such as temperature, pH and the like, are those previously used with QM-7 cells, and will be apparent to the ordinarily skilled artisan.

Transfection can be either transient or stable. Methods of carrying out transfections are known in the art. Stably transfected cells may be prepared by transfecting cells with an expression vector having a selectable marker gene (such as, e.g., the gene for thymidine kinase, dihydrofolate reductase, neomycin resistance, and the like), and growing the transfected cells under conditions selective for cells expressing the marker gene.

Either transiently or stably transfected QM-7 cells can be used in assays of uptake of $Ca^{++}$. Example IVb shows a typical assay (in this case, a real time, high throughput, $Ca^{++}$ imaging assay, using FLIPR) performed with transiently transfected cells. Example IVc shows such an assay performed with stably transfected cells.

In one aspect of the invention, QM-7 cells comprising a cell surface expressed channel receptor subunit (e.g., a mutant α7 polypeptide) are used to produce that polypeptide, in particular in a form in which the polypeptide (and/or the receptor in which it is located) remains associated (e.g., bound) to the membrane. Such a protein or a membrane-bound protein/receptor is useful, for example, for studying binding properties of the protein in in vitro assays, e.g., determining the affinity and/or specificity of a putative modulatory agent for the α7 polypeptide and/or membrane complex. Methods of harvesting and isolating such membrane-bound protein are conventional in the art. See, e.g., Davies et al. (1999), *Neuropharmacology* 38, 679-690.

The invention relates to a method (an assay) to detect transport of ions (cations) into a cell, comprising incubating a QM-7 cell of the invention in the presence of detectable ions, and detecting the presence of said ions in the cell. The ions can be, e.g., $Ca^{++}$, $Rb^+$ (e.g., $^{86}Rb^+$), $Na^+$, $K^+$, $Ba^{++}$, or other cations, preferably $Ca^{++}$ ions. The assay can be performed in the presence or absence (preferably the presence) of an appropriate α7 stimulatory ligand.

Methods for detecting such ions are conventional. For example, radioactively labeled ions, fluorescent ion-sensitive dyes, or dyes sensitive to membrane potential changes, can be detected. Also, reporter gene assays can be used, such as those described in Mattheakis et al. (2001), *Curr Opin Drug Discov Devel* 4 (1), 124-134. Among the suitable detection methods are fluoremetric imaging assays, in which the fluorescent signal of an ion (e.g., $Ca^{++}$)-sensitive dye is used to detect changes in intracellular levels of the ion (e.g., $Ca^{++}$). In a preferred embodiment, the assay makes use of a Fluorometric Imaging Plate Reader (FLIPR) provided by the Molecular Devices Corporation. This assay allows simultaneous detection of, e.g., $Ca^{++}$ signals from cells in, e.g., a 96- or 384-well format. Preferably, a method or an assay of the invention is a high throughput one.

Assays such as those described above, in which ion (e.g., $Ca^{++}$) influx is measured in QM-7 cells of the invention, can be used for a variety of purposes. For example, a test compound can be combined with a QM-7 cell of the invention, and it can be evaluated for its ability to elicit an appropriate response, e.g., influx of $Ca^{++}$, for its ability to inhibit the response of a cholinergic agent, or for its ability to modulate the response to an agonist or antagonist. Test compounds can be tested in desensitized QM-7 cells of the invention, or in cells in which channels are in the open state.

The invention relates to a method of screening agents to identify those agents that modulate (e.g., enhance, stimulate, restore, stabilize, increase, facilitate, up-regulate, activate, amplify, augment, induce, decrease, down-regulate, diminish, lessen, inhibit, block, reduce, destabilize, etc.) activity of an α7 subunit, or of a receptor comprising at least one such α7 subunit, comprising exposing a QM-7 cell comprising a mutant α7 polypeptide and/or nucleic acid, or a fragment or variant thereof, to a putative agent, in the presence or absence of an α7 stimulatory agent, and measuring the activity of the α7, e.g., as indicated by $Ca^{++}$ influx, compared to the activity in the absence of the putative agent.

As used herein, a compound or signal that "modulates the activity of a neuronal nicotinic AChR" refers to a compound or signal that alters the activity of NAChR so that activity of the NAChR is different in the presence of the compound or signal than in the absence of the compound or signal. In particular, such compounds or signals include agonists and antagonists. The term agonist refers to a substance or signal, such as ACh, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

A "nicotinic cholinergic agonist" is a compound that binds to and activates a nicotinic acetylcholine receptor. By "activates" is intended the elicitation of one or more pharmacological, physiological, or electrophysiological response. Such a response includes, but is not limited to, cell membrane depolarization and increased permeability to $Ca^{++}$ and other cations.

A "nicotinic cholinergic antagonist" is a substance that binds to a nicotinic acetylcholine receptor and prevents agonists from activating the receptor. Pure antagonists do not activate the receptor, but some substances may have mixed agonist and antagonist properties. Nicotinic cholinergic channel blockers block the ability of agonists to elicit current flow through the nicotinic acetylcholine receptor channel, but do so by blocking the channel rather than by preventing agonists from binding to an activating the receptor.

A "nicotinic cholinergic regulator" intends a substance that influences the activity of the nicotinic acetylcholine receptor through interaction at one or more sites other than the classic agonist binding site. The regulator may itself increase or decrease receptor activity, or may influence agonist activity (for example, potentiating responses) without itself eliciting on overt change in channel current. A single substance can have different properties at different nicotinic acetylcholine receptor subtypes, for example, being an agonist at one receptor and antagonist at another, or an antagonist at one and a channel blocker at another.

By "nAChR modulator" is intended a substance that may act as an agonist, antagonist, channel blocker or regulator.

As understood by those of skill in the art, assay methods for identifying compounds that modulate human neuronal nicotinic ACHR activity (e.g., agonists and antagonists) generally require comparison to a control. One type of a "control" cell or "control" culture is a cell or culture that is treated substantially the same as the cell or culture exposed to the test compound, except the control culture is not exposed to test compound. Another type of "control" cell or "control" culture may be a cell or a culture of cells which are identical to the transfected cells, except the cells employed for the control culture express the wild type α7 receptor instead of a mutant α7 receptor of the invention. In this situation, the response of test cell to test compound is compared to the response (or lack of response) control to test compound, when cells or cultures of each type of cell are exposed to substantially the same reaction conditions in the presence of compound being assayed.

In another embodiment, the invention relates to a method of screening agents to identify those agents which modulate (e.g., enhance, stimulate, restore, stabilize, increase, facilitate, up-regulate, activate, amplify, augment, induce, decrease, down-regulate, diminish, lessen, inhibit, block, reduce, destabilize, etc.) expression of an α7 subunit. To assay for agents that regulate expression of QM-7 regulatory elements (e.g., the promoter or enhancer), a QM-7 cell comprising a mutant α7 of the invention that has been placed under the control of a wild type α7 regulatory element (e.g., promoter and/or enhancer) is exposed to a putative agent, and the uptake of $Ca^{++}$ into the cell is monitored as a measure of the amount of the mutant α7 produced. To assay for agents that regulate other facets of α7 gene expression, such as splicing, other cloned sequences, e.g., intron-containing constructs as described elsewhere herein, can be used in such an assay. Thus, the invention relates to a method to identify a modulator of α-7 expression, comprising testing a putative modulator for its ability to increase or decrease $Ca^{++}$ transport in a QM-7 cell containing a mutant α7 of the invention, or functional fragment or variant thereof, which is under the control of one or more appropriate α7 regulatory elements, compared to the amount of $Ca^{++}$ transport in the absence of the putative modulator.

In another embodiment, the invention relates to a method of screening agents to identify those agents that modulate (e.g., enhance, stimulate, restore, stabilize, increase, facilitate, up-regulate, activate, amplify, augment, induce, decrease, down-regulate, diminish, lessen, inhibit, block, reduce, destabilize, etc.) the transport of an α7 subunit, or of a receptor comprising at least one such α7, subunit, to the cell membrane, comprising exposing a QM-7 cell comprising a mutant α7 polypeptide and/or nucleic acid, or a fragment or variant thereof, to a putative agent, in the presence or absence of an α7 stimulatory agent; isolating cell membranes from said exposed cell, using conventional, art-recognized, procedures; and measuring the amount of the α7 in the isolated cell membranes, compared to the amount in the absence of the putative agent.

Methods and assays of the invention can also be used for experimental purposes, e.g., to study the mechanism of action of α7 AChR's and/or the association of the α7 AChR subunits and/or the association of the α7 subunit with other proteins.

Assays for $Ca^{++}$ uptake can be performed either in the absence of a ligand or following stimulation by an appropriate ligand. Appropriate stimulatory ligands include, e.g., nicotine or nicotinic acid (preferably the—enantiomer), carbamyl choline, cytisine, acetylcholine, epibatidine, or α7-specific ligands, such as GTS-21, 4-OH-GTS-21. Non α7-specific ligand stimulation can be shown by the reduction or blocking of the signal with conventional inhibitors such as, e.g., Methyllycaconitine or alpha-Bungarotoxin, but not with Mecamylamine.

Among the types of modulatory agents that can be tested and identified by the methods of the invention are, e.g., small chemical compounds (e.g., inorganic or organic molecules, such as conventional combinatorial libraries), polypeptides, peptides or peptide analogs, polynucleotides, antibodies that bind specifically to the polypeptides of the invention, or the like.

Without wishing to be bound to any particular mechanism, it is proposed that an inhibitory or stimulatory agent may act on the ligand binding moiety of the α7 receptor, on an allosteric binding moiety, or on an element of the ion channel, thereby modulating activity of the protein; or the agent may enter cells and, e.g., bind directly to the DNA neighboring the sequences coding for the polypeptides of the invention, thereby increasing or decreasing their expression; or the agent may enter the cell and affect post-transcriptional processing, thereby modulating protein activity; or the agent may affect the transport of the α7 to the cell membrane.

Agonists (including partial agonists) of the α7 receptor obtained by the methods of the invention may be used to treat, prevent, and/or ameliorate the symptoms of diseases or conditions associated with reduced expression and/or activity of receptors comprising one or more α7 subunits, e.g., conditions associated with reduced nicotine transmission. For example, such agonists can be used to treat alterations in sensory gating; neuropathic pain (e.g., pain associated with cancerous conditions, post herpatic neuralgia, diabetic neuropathy and osteoarthritis); neurodegenerative disorders, including, e.g., kuru, Alzheimer's Disease, Down's syndrome, Parkinson's disease; affective disorders; MCI (mild cognitive impairment) or other age-related cognitive impairment; sensory processing related to schizophrenia or psychosis; myasthenia gravis; ADNFLE; attention deficit hyperactivity disorders; depression; mania and manic depression; jetlag; nicotine addiction (including that resulting from exposure to products containing nicotine, e.g.,  smoking cessation); Tourette's syndrome; or other processes related to function of the central nervous system, such as anxiety; and to enhance memory, learning, cognition, attention, enzymatic function, immunofunction, cytoprotection (e.g., protection from β-amyloid toxicity or other amyloidosis), or neurite outgrowth and innervation. The skilled worker will recognize a variety of other conditions related to the function of receptors comprising the α7 subunit that can be treated with such agonists.

Antagonists of the α7 receptor obtained by the methods of the invention may be useful for treatment of any of the conditions mentioned above. Furthermore, such antagonists are useful, e.g., as tools for studying the binding of other modulatory agents. For example, competition assays can be performed in which such an antagonist is presented to a cell in the presence of a partial agonist, and the degree to which the partial agonist is inhibited is determined.

Any of the assays described herein can, of course, be adapted to any of a variety of high throughput methodologies, as can the generation, identification and characterization of putative inhibitory or stimulatory agents.

Another aspect of the invention is a kit comprising a QM-7 cell that comprises a mutant α7 of the invention; a $Ca^{++}$ sensitive dye, appropriate buffer and, optionally, positive controls, such as, e.g., GTS-21 or nicotine, and/or negative controls, such as QM-7 cells containing wild type α7 or containing no α7 protein.

Figure 1:
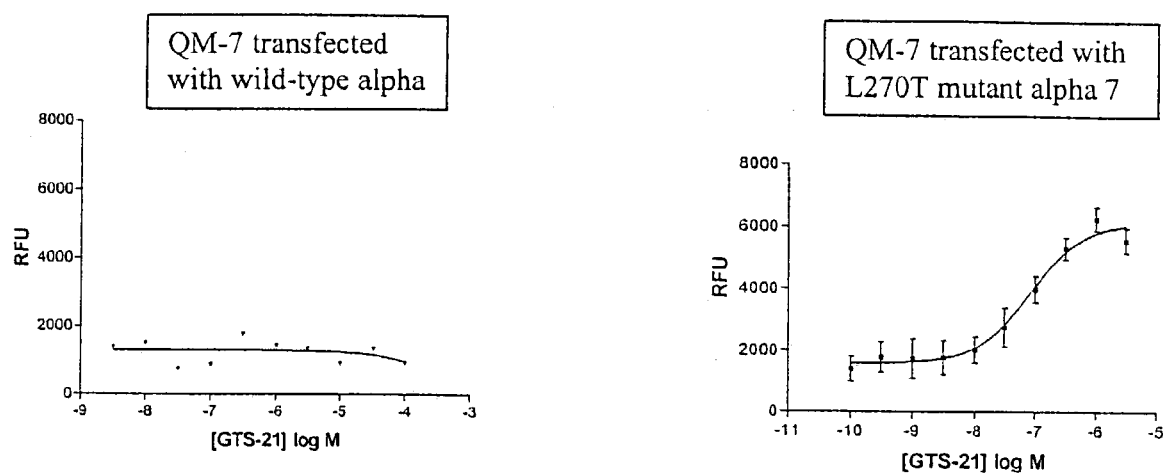
FIG. 1 shows assays, using FLIPR, that compare $Ca^{++}$ signal in QM-7 cells that are transiently transfected by either wild type or human L270T α7.

In the foregoing and in the following examples, all temperatures are set forth uncorrected in degrees Celsius; and, unless otherwise indicated, all parts and percentages are by weight.

EXAMPLES

Example I

Construction of Human Alpha 7 Mutation L270T

Wild type human alpha 7 coding sequence was PCR amplified from human hippocampus cDNA (Clontech) and cloned into Invitrogen expression vector pcDNA 3.1 V5/His TOPO. The clones containing the PCR fragment in the right orientation (5'end downstream of CMV promoter) were chosen and sequenced. The clone shown to encode an identical protein sequence to published human alpha 7 sequence was used to construct L270T mutant.

To create the L270T mutant, the following primers were used to mutagenize wild type human alpha 7:

```
HSAlpha7-14:    5'GGGATAACAGTCTTAACTTCTCTTACCGTCTTCATGCTGCTCCGTG (SEQ ID NO: 1)
            3'

HSAlpha7- 15: 5'TGAAGACGGTAAGAGAAGTTAAGACTGTTATCCCCAGGGAAATCTTCTCC (SEQ ID NO: 2)
3'
```

The mutagenesis and PCR reactions were performed using QuickChange site-directed mutagenesis kit (Stratagene) according to the protocol from the manufacture.

One clone was sequence verified to contain the desired mutation L270T as shown below and used for the experiments shown in Example IV.

```
GGGCGACAGCCGAGACGTGGAGCGCGCCGGCTCGCTGCAGCTCCGGGACTCAACATGCGCTGCTC (SEQ ID NO: 3)
GCCGGGAGGCGTCTGGCTGGCGCTGGCCGCGTCGCTCCTGCACGTGTCCCTGCAAGGCGAGTTCC
AGAGGAAGCTTTACAAGGAGCTGGTCAAGAACTACAATCCCTTGGAGAGGCCCGTGGCCAATGAC
TCGCAACCACTCACCGTCTACTTCTCCCTGAGCCTCCTGCAGATCATGGACGTGGATGAGAAGAA
CCAAGTTTTAACCACCAACATTTGGCTGCAAATGTCTTGGACAGATCACTATTTACAGTGGAATG
TGTCAGAATATCCAGGGGTGAAGACTGTTCGTTTCCCAGATGGCCAGATTTGGAAACCAGACATT
CTTCTCTATAACAGTGCTGATGAGCGCTTTGACGCCACATTCCACACTAACGTGTTGGTGAATTC
TTCTGGGCATTGCCAGTACCTGCCTCCAGGCATATTCAAGAGTtcCTGCTACATCGATGTACGCT
GGTTTCCCTTTGATGTGCAGCACTGCAAACTGAAGTTTGGGTCCTGGTCTTACGGAGGCTGGTCC
TTGGATCTGCAGATGCAGGAGGCAGATATCAGTGGCTATATCCCCAATGGAGAATGGGACCTAGT
GGGAATCcccGGCAAGAGGAGTGAAAGGTTCTATGAGTGCTGCAAAGAGCCCTACCCCGATGTCA
CCTTCACAGTGACCATGCGCCGCAGGACGCTCTACTATGGCCTCAACCTGCTGATCCCCTGTGTG
CTCATCTCCGCCCTCGCCCTGCTGGTGTTCCTGCTTCCTGCAGATTCCGGGGAGAAGATTTCCCT
GGGGATAACAGTCTTAaCTtCTCTTACCGTCTTCATGCTGCTCGTGGCTGAGATCATGCCCGCAA
CATCCGATTCGGTACCALTGATAGCCCAGTACTTCGCCAGCACCATGATCATCGTGGGCCTCTCG
GTGGTGGTGACAGTGATCGTGCTGCAGTACCACCACCACGACCCCGACGGGGGCAAGATGCCCAA
GTGGACCAGAGTCATCCTTCTGAACTGGTGCGCGTGGTTCCTGCGAATGAAGAGGCCCGGGGAGG
ACAAGGTGCGCCCGGCCTGCCAGCACAAGCAGCGGCGCTGCAGCCTGGCCAGTGTGGAGATGAGC
GCCGtGGCGCCGCCGCCCGCCAGCAACGGGAACCTGCTGTACATCGGCTTCCGCGGCCTGGACGG
CGTGCACTGTGTCCCGACCCCCGACTCTGGGGTAGTGTGTGGCCGCATGGCCTGCTCCCCCACGC
ACGATGAGCACCTCCTGCACGGTGGGCAACCCCCCGAGGGGGACCCGGACTTGGCCAAGATCCTG
GAGGAGGTCCGCTACATTGCCAACCGCTTCCGCTGCCAGGACGAAAGCGAGGCGGTCTGCAGCGA
GTGGAAGTTCGCCGCCTGTGTGGTGGACCGCCTGTGCCTCATGGCCTTCTCGGTCTTCACCATCA
TCTGCACCATCGGCATCCTGATGTCGGCTCCCAACTTCGTGGAGGCTGTGTCCaAAGACTTTGCG
TAACCACGCCTGGTTCTGTACATGTGGAAAACTCACAGATGGGCAaGGCCTTtGGCTTGGCGAGA
TTTGGGGGTGC
``` protein:

MRCSPGGVWLALAASLLHVSLQGEFQRKLYKELVKNYNPLERPVANDSQPLTVYFSLSLLQIMDV (SEQ ID NO: 4)

DEKNQVLTTNTWLQMSWTDHYLQWNVSEYPGVKTVRFPDGQIWKPDTLLYNSADERFDATFHTNV

LVNSSGHCQYLPPGIFKSSCYTDVRWFPPDVQHCKLKFGSWSYGGWSLDLQMQEADISGYTPNGE

WDLVGIPGKRSERFYECCKEPYPDVTFTVTMRRRTLYYGLNLLIPCVLISALALLVFLLPADSGE

KTSLGTTVLTSLTVFMLLVAEIMPATSDSVPLIAQYFASTMTTVGLSVVVTVIVLQYHHHDPDGG

KMPKWTRVILLNWCAWFLRMKRPGEDKVRPACQHKQRRCSLASVEMSAVAPPPASNGNLLYTGFR

-continued

GLDGVHCVPTPDSGVVCGRMACSPTHDEHLLHGGQPPEGDPDLAKILEEVRYIANRFRCQDESEA

VCSEWKFAACVVDRLCLMAFSVFTITCTIGILMSAPNFVEAVSKDFA

Alignment of M2 domain: human wild type alpha 7 vis L270T mutant

```
      260         270         280
S G E K I S L G I T V LL S L TVF M LLV A E I M Wildtype alpha 7 (SEQ ID NO: 5, SEQ ID NO: 6)
S G E K I S L G I T V L T  S L TVF MLLV A EI M L270T
    --------------------------------
              MII domain
```

Example II

Construction of Rat Alpha 7 Mutation L270T

Wild type rat alpha 7 coding sequence was PCR amplified from rat brain cDNA and cloned into Invitrogen expression vector pcDNA 3.1 V5/His TOPO. The clones containing the PCR fragment in the right orientation (5'end downstream of CMV promoter) were chosen and sequenced. The clone shown to encode an identical protein sequence to published rat alpha 7 sequence (Seguela, P. et al. Molecular cloning, functional properties, and distribution of rat brain alpha 7: a nicotinic cation channel highly permeable to calcium. J. Neurosci. 13(2), 596-604 (1993)) was used to construct L270T mutant.

To create the L270T mutant, the following primers were used to mutagenize wild type rat alpha 7:

```
RNAlpha7-muF: 5'CTCTTGGAATAACTGTCTTAACTTCTCTGACTGTCTTCATGC    (SEQ ID NO:7)
3'

RNAlpha7-muR: 5'GCATGAAGACAGTCAGAGAAGTTAAGACAGTTATTCCAAGAG 3'  (SEQ ID NO: 8)
```

The mutagenesis and PCR reactions were performed using QuickChange site-directed mutagenesis kit (Stratagene) according to the protocol from the manufacture.

One clone was sequence verified to contain the desired mutation L270T as shown below.

(SEQ ID NO: 9)
```
CCACCATGTGCGGCGGGCGGGGAGGCATCTGGCTGGCTCTGGCCGCGGCGCTGCTGCACGTGTCCCTGCAAGGCGAGTTC
CAGAGGAGGCTGTACAAGGAGCTGGTCAAGAACTACAACCCGCTGGAGAGGCCGGTGGCCAACGACTCGCAGCCGCTCAC
CGTGTACTTCTCCCTGAGTCTCCTGCAGATCATGGATGTGGATGAGAAGAACCAAGTTTTAACCACCAACATTTGGCTAC
AAATGTCTTGGACAGATCACTATTTGCAGTGGAACATGTCTGAGTACCCCGGAGTGAAGAATGTTCGTTTTCCAGATGGC
CAGATTTGGAAACCAGACATTCTCCTCTATAACAGTGCTGATGACCGCTTTGATGCCACGTTCCACACCAATGTTTTGGT
GAATGCATCTGGCCATTGCCAGTATCTCCCTCCAGGCATATTCAAGAGCTCCTGCTACATTGACGTTCGCTGGTTCCCTT
TTGATGTCCAGCAGTGCAAACTGAAGTTTGGGTCCTGGTCCTATGGAGGGTGGTCACTGGACCTGCAAATGCAAGAGGCA
GATATCACCAGCTATATCCCCAACGGAGAATGGGATCTCATGGGAATCCCTGGCAAAAGGAATGAGAAGTTCTATGAGTG
CTGCAAAGAGCCATACCCAGATGTCACCTACACAGTAACCATGCGCCGTAGGACACTCTACTATCGCCTCAATCTGCTCA
TCCCTTGTGTACTCATTTCACCCCTGGCTCTGCTGGTATTCTTGCTGCCTGCAGACTCTGGAGAGAAAATCTCTCTTGGA
ATAACTGTCTTAACTTCTCTGACTGTCTTCATGCTGCTTCTGGCTGAGATCATGCCAGCAACATCTGATTCTGTGCCCTT
GATAGCACAATACTTCGCCAGCACCATGATCATCGTGGGCCTCTCTGTAGTGGTGACAGTGATTGTGCTGAGATATCACC
ACCATGACCCTCATGGTGGCAAAATGCCTAAGTGGACCAGAATCATTCTCCTGAACTGGTGTGCATGGTTTCTGCGCATG
AAGAGGCCCGGAGAGGACAAGGTCCGGCCAGCTTGTCAGCACAAGCCTCGGCGCTGCAGCCTGGCCAGTGTGGAGCTGAG
TGCAGGTGCTGGGCCACCCACCAGCAATGGCAACCTGCTCTACATTGGCTTCCCAGGCCTGGAGGGCATGCACTGTGCCC
CAACTCCAGACTCTGGGGTCGTATGTGGCCGTTTGGCCTGCTCCCCAACACATGATGAGCACCTCATGCACGGTGCACAC
CCCTCTGATGGGCACCCCGACCTGGCCAAGATCCTGGAGGAGGTCCGCTACATCGCCAACCGCTTCCGCTGCCAGGACGA
GAGTGAGGTGATCTGCAGTGAATGGAAGTTTGCAGCCTGCGTGGTGGACCGCTTGTGCCTCATGGCCTTTTCGGTCTTTA
CCATCATCTGTACCATCGGCATCCTCATGTCAGCTCCAAACTTTGTGGAGGCTGTGTCCAAAGACTTTGCTTAATGTTAT
CAAGTAGGAAATGCGCAGATAAGAAGAGAATCTGGAGGGTGAGAATTGGGG
```

Protein:

(SEQ ID NO: 10)
```
MCGCRGGIWLALAAALLHVSLQGEFQRRLYKELVKNYNPLERPVANDSQPLTVYFSLSLLQIMDVDEKNQVLTTNIWLQM
SWTDHYLQWNNSSYPGVKNVRPPDGQIWKPDILLYNSADERFDATFHTNVLVNASGHCQYLPPGIFKSSCYIDVRWFPFD
VQQCKLKFGSWSYGGWSLDLQMQEADISSYIPNGEWDLMGIPGKRNEKFYECCKEPYPDVTYTVTMRRRTLYYGLNLLIP
CVLISALALLVFLLPPDSGEKISLGITVLTSLTVFMLLVAEIMPATSDSVPLIAQYFASTMIIVGLSVVVTVIVLRYHHH
DPDGGKNPKWTRIILLNWCAWFLRNKRPGSDKVRPACQHKPRRCSLASVELSAGAGPPTSNGNLLYIGFRGLEGMHCAPT
PDSGVVCGRLACSPTHDEHLMHGAHPSDGPDLAKILEEVRYIANRFRCQDESEVICSEWKFAACVVDRLCLMAPSVFTI
ICTIGILMSAPMFVEAVSKDFA
```

Example III a) Full Length Cloning of Rhesus Monkey Alpha 7

1) RACE the 5'-, 3'-Ends of Rhesus Monkey Alpha 7

A Gene Racer cDNA library was generated using rhesus monkey brain mRNA (Biochain) according to the standard protocol (Invitrogen). Four primers, mk α 7-5'R, mk α 7-5'N, mk α 7-3'R and mk α 7-3'N, were designed based on Genbank sequence AJ245976 and used to PCR the 5' and 3' ends sequences of rhesus monkey alpha 7.

```
RACE primers
mk α7-5'R:     5'CTCATCTCCACGCTGGCCAGGTGCAG 3'        (SEQ ID NO: 11)

mk α7-3'R:     5'CATGAAGAGGCCGGGAGAGGATAAGGTGCG 3'    (SEQ ID NO: 12)

Nest primers
mk α7-5'N:     5'CGCACCTTATCCTCTCCCGGCCTCTTCATG 3'    (SEQ ID NO: 13)

mk α7-3'N:     5'CTGCACCTGGCCAGCGTGGAGATGAG 3'        (SEQ ID NO: 14)
```

5' and 3' RACE PCR reactions were performed on rhesus monkey brain cDNA library using mk α 7-5'R, mk α 7-3'R and Gene Racer 5'-, 3'-RACE primers respectively. The PCR reactions were carried out using PCRx system and platinum HF polymerase (Invitrogen) with the following cycling characteristics: 94° C. for 3' for 1 cycle; 94° C. for 30" and 68° C. for 1'30" for 35 cycles; 68° C. for 7' for 1 cycle. After PCR, the resulting fragments were used as templates for nested PCR using mk α 7-5'N, mk α 7-3'N and Gene Racer 5'-, 3'-Nest primers respectively. The nested PCR protocol was the same as the RACE PCRs.

The nested PCR products were then column purified (Qiagen) and cloned into pcDNA3.1 v5/his TOPO vector and sequenced.

One clone, named mk-3'N#2, contains the 3' end of rhesus monkey alpha 7 and is listed below (A). Another clone, named mk α 7-5'N#13, contains the incomplete 5' end of rhesus monkey alpha 7 and is listed below (B).

To obtain the complete 5' end sequence of rhesus monkey alpha 7, two primers, mk α 7-5'R1 and mk α 7-5'N1, were designed according to the sequence of mk α 7-5'N#13 and used to PCR the same cDNA library as described above, yet with the following cycling characteristics: 94° C. for 3' for 1 cycle; 94° C. for 30", 65° C. for 30" and 68° C. for 1' for 35 cycles; 68° C. for 7' for 1 cycle. The nested PCR products were then column purified (Qiagen) and cloned into pcDNA3.1 v5/his TOPO vector and sequenced.

```
RACE primer
mk α7-5'R1:                              (SEQ ID NO: 17)
5'GACCAGCCTCCATAAGACCAGGATCCAAACTTCAG 3'

Nest primer
mk α7-5'N1:                              (SEQ ID NO: 18)
5'CGCACGTCGATGTAGCAGGAACTCTTGAATATGC 3'
```

A. mk-3'N#2: the 3'stop codon and poly A+signal were bolded.

(SEQ ID NO: 15)
CTGCAGCCTGGCCAGCGTGGAGATGAGCGCCGTGGCGCCGCCGCCTCCCAGCAACGGGAACCTGCTGTACATCGGCTTCC

GCGGCCTGGACGGCATGCATTGCGCCCCGACCCCCGACTCCGGGGTGGTGTGCGCCCCCATGGCCTGCTCCCCCACGCAC

GACGAGCACCTCCTGCACGGTGGGCAGCCCCCCGAGGCGGACCCGGACCTGGCCAAGATCCTGGAGGAGGTCCGCTACAT

CGCCAACCGCTTTCGCTGCCAGGACGAAACCGAGGCGGTCTGCAGCGAGTGGAAGTTCGCCGCCTGCGTGGTGCACCGCC

TGTGCCTCATGGCCTTCTCGGTCTTCACCATCATCTGCACCATCGGCATCCTGATGTCGGCTCCCAACTTCGTGGAGGCC

GTGTCCAAAGACTTTGCGTAACCACGCCTGGTTCTGTACATGTGGAAAACTCACAGATGGGCAAGGCCTCTGGCTTGGTG

AGATTTTGGGGTGCTAATCCAGGACAACATTAAACGCCACAACTCCGATGTTCCCTTCTGGCTGTCAGTCGTGTCGCTCA

CGGTTTCCTCATTACTTTAGGTAGTAGGATCTCAGCACTCAGTTTAATACGCTCAGGTGGGCTGATCATCCCCTTGGCAC

ATCCGCACTGTCGGTCAGCAGGGCCACTGAGAAGTCATTTTGCCCATTAGCCCACTGCCTGGAAAGCCCTTCAGAGAGCT

CCCAGTGGCTCCTCACCCCGGGACAGTTGGTTTTGCATGTCTGCATGCCACTTGCCATGAAGGCCTACCTGAAAATTCAA

CATTTGCTTTTTGCTTGTGTACAAACCTAGATTGAAGCTAAAATAAACCAGACTCACTAAATCCAAAAAAAAAAAAAAAA

B. mk α7-5'N#13:

(SEQ ID NO: 16)
GTATTTTGAGCGCGTCTCGATCAGCTTTCGTTTCAGTCTTCTGTTTCCGTCACCCACACGGGCATATTCAAGAGTTCCTG

CTACATCGACGTGCGCCGGTTTCCCTTTGATGTGCAGCATTGCAAACTGAAGTTTGGATCCTGGTCTTATGGAGGCTGGT

CCTTGGATCTGCAGATGCAGGAGGCAGATATCAGTGGCTATATCCCCAGTGGAGAATGGGACCTAGTGGGAATTCCCGGC

AAGAGGAGTGAAAAGTTCTATGAGTGCTGCAAAGAGCCCTACCCCGATGTCACCTTCACAGTGACCATGCGCCGCAGGAC

CCTCTACTACGGCCTCAACCTGCTCATCCCCTGTGTGCTCATCTCTGCCCTTGCCCTGCTGGTCTTCCTGCTTCCTGCAG

ATTCCGGGGAGAAGATTTCCCTGGGGATAACAGTCTTACTCTCTCACTGTCTTCATGCTGCTCGTGGCTGAGATCATG

CCCGCAACATCTGATTCAGTACCATTGATAGCCCAGTACTTCGCCAGCACCATGATCATCGTGGGCCTCTCCGTGGTGGT

GACGGTGATCGTGCTGCAGTACCACCACCACGACCCCGACGGGGCAAGATGCCCAAGTGGACCAGAGTCATCCTTCTGA

ACTGGTCCGCGTGGTTCCTGCGCATGAAGAGGCCGGGAGAGGATAAGGTGCG

One clone, named mk α 7#1, still only contains the incomplete 5' end of rhesus monkey alpha 7 and is listed below.

mk α7#1:
(SEQ ID NO: 19)
CATTGCCGGCATCTGTCCTCCCCGACAGGGTGCCTCCAGCACTTCAGATCCCACCCGAGAGTCTGGCTGCTACCGCCCAG

CAAACGTGTCCCTGCAAGGCGAGTTCCAGAGGAAGCTTTACAAGGAGCTGGTCAAGAACTACAACCCCTTGGAGAGGCCC

GTGGCCAATGACTCGCAACCGCTCACCGTCTACTTCTCCCTGAGCCTCCTGCAGATCATGGACGCGGATGAGAAGAACCA

AGTTTTAACCACCAACATTTGGCTGCAAATGTCTTGGACAGATCACTATTTACAGTGGAATGTGTCAGAATATCCAGGGG

TGAAGACTGTTCGTTTCCCAGATGGCCAGATTTGGAAACCAGACATTCTTCTCTATAACAGTGCGGATGAGCGCTTTGAC

GCCACATTCCACACCAACGTGTTGGTGAATTCTTCTGGGCATTGCCAGTACCTCCCTCCAGGCATATTCAAGAGTTCCTG

CTAATCGACGTGCG

Again, to obtain the complete 5' end sequence of rhesus monkey alpha 7, two more primers, mk a 7-5'R2 and mk a 7-5'N2, were designed according to the sequence of mk a 7#1 and used to PCR the same cDNA library as described above, yet with the following cycling characteristics: 94° C. for 5' for 1 cycle; 94° C. for 20", 65° C. for 20" and 68° C. for 30", for 35 cycles; 68° C. for 7' for 1 cycle. The nested PCR products were then column purified (Qiagen) and cloned into pcDNA3.1 v5/his TOPO vector and sequenced.

One clone, named mk α 7-5'N#16, contains the 5' Met of rhesus monkey alpha 7 and is listed below.

mk α7-5'N#16: the starting Met is bolded
(SEQ ID NO: 20)
GAGAGGCGGCTCTGTGGCCACAGGCGCAGCCCCGCGCGACAGCCGATACGTGAGGCGCGCCGGCCCGCGGCAGCTCCGGG

ACTCAACATGCGCTGCTCGCAGGGAGGCGTCTGGCTGGCTCTGGCCCCGTCGCTCCTGCATGTGTCCCTGCAAGGCGAGT

TCCAGAGGAAGCTTTACAAGGAGCTGGTCAAGAACTACAACCCCTTGGAGAGGCCCGTGGCCAATGACTCGCAACCGCTC

ACCGTCTAC

2) Full-Length Cloning of Rhesus Monkey Alpha 7

Two primers, mk α 7-5'b and mk α 7-3'a, were designed based on the sequences of mk α 7-5'N#16 and mk-3'N#2 (see above) and used to PCR full-length rhesus monkey alpha 7 from the same cDNA library.

mk α7-5'b:
5'CTCAACATGCGCTGCTCGCAGGGAGG 3'    (SEQ ID NO: 21)

mk α7-3'a:
5'CCAAGCCAGAGGCCTTGCCCATCTGTGAG 3' (SEQ ID NO: 22)

The PCR reaction was performed as described above with the following cycling characteristics: 94° C. for 5' for 1 cycle; 94° C. for 30", 65° C. for 30" and 68° C. for 2' for 35 cycles; 68° C. for 7' for 1 cycle. The resulting PCR fragment (~1.6 kb) was column purified (Qiagen) and cloned into pcDNA3.1 v5/his TOPO vector and sequenced.

One clone, named mkalpha7#11, contained the full-length cDNA sequence of rhesus monkey alpha 7. The cDNA and protein sequences are listed below. This clone, with the 5' Met of the full-length rhesus monkey alpha 7 is downstream of the vector CMV promoter, can be used to establish stable cell line to expressed the recombinant receptor.

cDNA sequence of full-length rhesus monkey alpha 7 (mkalpha7#11):

(SEQ ID NO: 23)
CTCAACATGCGCTGCTCGCAGCGAGGCGTCTGGCTGGCTCTGGCCGCGTCGCTCCTGCATGTGTCCCTGCAAGGCGAGTT
CCAGAGGAAGCTTTACAAGGAGCTGGTCAAGAACTACAACCCCTTGGAGAGGCCCGTGGCCAATGACTCGCAACCGCTCA
CCGTCTACTTCTCCCTGAGCCTCCTGCAGATCATGGACGTGGATGAGAAGAACCAAGTTTTAACCACCAACATTTGGCTG
CAAATGTCTTGGACAGATCACTATTTACAGTGGAATGTGTCAGAATATCCAGGGGTGAAGACTGTTCGTTTCCCAGATGG
CCAGATTTGGAAACCAGACATTCTTCTCTATAACAGTGCGGATGAGCGCTTTGACGCCACATTCCACACCAACGTGTTGG
TGAATTCTTCTGGGCATTGCCACTACCTGCCTCCAGGCATATTCAAGAGTTCCTGCTACATCGACGTGCGCTGGTTTCCC
TTTGATGTGCAGCATTGCAAACTGAAGTTTGGATCCTGGTCTTATGGAGCCTGGTCCTTGGATCTGCAGATGCAGGAGGC
AGATATCAGTGGCTATATCCCCAGTGGAGAATGGGACCTAGTGGGAATTCCCGGCAAGAGGAGTGAAAAGTTCTATGAGT
GCTGCAAAGAGCCCTACCCCGATGTCACCTTCACAGTGACCATGCGCCGCAGGACCCTCTACTACGCCTCAACCTGCTG
ATCCCTGTGTGCTCATCTCTGCCCTTGCCCTGCTGGTGTTCCTGCTTCCTGCAGATTCCGGGGAGAAGATTTCCCTGGG
GATAACAGTCTTACTCTCTCACTGTCTTCATGCTGCTCGTGGCTGAGATCATGCCCGCAACATCTGATTCAGTACCAT
TGATAGCCCAGTACTTCGCCAGCACCATGATCATCGTGGGCCTCTCGGTGGTGGTGACGGTGATCGTGCTGCAGTACCAC
CACCACGACCCCGACGGGGGCAAGATGCCCAAGTGGACCAGAGTCATCCTTCTGAACTGGTGCGCGTGGTTCCTGCGCAT
GAAGAGGCCCGGAGAGGATAAGGTGCGCCCGGCCTGCCAGCACAACCAGCGCCGCTGCAGCCTGGCCAGCGTGGAGATGA
GCGCCGTGGCGCCGCCGCCTGCCAGCAACGGGAACCTGCTGTACATCGGCTTCCCCGGCCTGCACGGCATGCATTGCGCC
CCGACCCCCGACTCCGGGGTGGTGTGCGGCCGCATGGCCTGCTCCCCCACGCACGACGAGCACCTCCTGCACGGTGGGCA
GCCCCCCGAGGGGGACCCGGACCTGGCCAAGATCCTGGAGGAGGTCCGCTACATCGCCAACCGCTTTCGCTGCCAGGACG
AAAGCGAGGCGGTCTGCAGCGAGTGCAAGTTCGCCGCCTGCGTGGTGGACCGCCTGTGCCTCATGGCCTTCTCGGTCTTC
ACCATCATCTGCACCATCGGCATCCTGATGTCGGCTCCCAACTTCGTGCAGGCCGTGTCCAAAGACTTTGCGTAACCACG
CCTGGTTCTGTACATGTGGAAAACTCACAGATGGGCAAGGCCTCTGGCTTG b) Construction of Rhesus Monkey Alpha 7 Mutation L270T To create the L270T mutant, the following primers were used to mutagenize wild type rhesus monkey alpha 7:

```
mk α7-14:                        (SEQ ID NO: 24)
5'GGGATAACAGTCTTAACTTCTCTCACTGTCTTC 3' mk α7-15:                        (SEQ ID NO: 25)
5'GAAGACAGTGAGAGAAGTTAAGACTGTTATCCC 3'
```

The mutagenesis and PCR reactions were performed using QuickChange site-directed mutagenesis kit (Stratagene) according to the protocol from the manufacture.

One clone was sequence verified to contain the desired mutation L270T as shown below.

(SEQ ID NO: 26)
CTCAACATGCGCTGCTCGCAGGGAGGCGTCTGGCTGGCTCTGGCCGCGTCGCTCCTGCATGTGTCCCTGCAAGGCGAGTT
CCAGAGGAAGCTTTACAAGGAGCTGGTCAAGAACTACAACCCCTTGGAGAGGCCCGTGCCCAATGACTCGCAACCGCTCA
CCGTCTACTTCTCCCTCAGCCTCCTGCAGATCATGGACGTGGATGAGAAGAACCAAGTTTTAACCACCAACATTTGGCTG
CAAATGTCTTGGACAGATCACTATTTACAGTGGAATGTGTCAGAATATCCAGGGGTGAAGACTGTTCGTTTCCCAGATGG
CCAGATTTGCAAACCAGACATTCTTCTCTATAACAGTGCGGATGAGCGCTTTGACGCCACATTCCACACCAACGTCTTCG
TGAATTCTTCTGGGCATTGCCAGTACCTGCCTCCAGGCATATTCAAGAGTTCCTGCTACATCCACGTGCGCTGGTTTCCC
TTTGATGTGCAGCATTGCAAACTGAAGTTTGGATCCTGGTCTTATGGAGGCTGGTCCTTGGATCTGCAGATGCAGGAGGC
AGATATCAGTGGCTATATCCCCAGTGGAGAATGGGACCTAGTGGGAATTCCCGGCAAGAGGAGTGAAAAGTTCTATGAGT
GCTGCAAAGAGCCCTACCCCCATGTCACCTTCACAGTGACCATGCGCCGCAGGACCCTCTACTACGCCTCAACCTGCTG
ATCCCTGTGTGCTCATCTCTGCCCTTGCCCTGCTGGTGTTCCTGCTTCCTGCAGATTCCGGGGAGAAGATTTCCCTCGC

-continued
```
GATAACAGTCTTAACTTCTCTCACTGTCTTCATGCTGCTCGTGGCTGAGATCATGCCCGCAACATCTGATTCAGTACCAT

TGATAGCCCAGTACTTCGCCAGCACCATGATCATCGTGGGCCTCTCGGTGGTGGTGACGGTGATCGTGCTGCAGTACCAC

CACCACGACCCCGACGGGGGCAAGATGCCCAAGTGGACCAGAGTCATCCTTCTGAACTGGTGCGCGTGGTTCCTGCGCAT

GAAGAGGCCCGGAGAGGATAAGGTGCGCCCGGCCTGCCAGCACAAGCAGCGCCGCTGCAGCCTGGCCAGCGTGGAGATGA

GCGCCGTGGCGCCGCCGCCTGCCAGCAACGGGAACCTGCTGTACATCCGCTTCCGCGGCCTGGACGGCATGCATTGCGCC

CCGACCCCCGACTCCGGGGTGGTGTGCGGCCGCATGGCCTGCTCCCCCACGCACGACGAGCACCTCCTGCACGGTGGGCA

GCCCCCCGAGGGGGACCCGGACCTCGCCAAGATCCTGGAGGAGGTCCGCTACATCGCCAACCGCTTTCGCTGCCAGGACG

AAAGCGAGCCGGTCTGCAGCGAGTGGAAGTTCGCCGCCTGCGTGGTGGACCGCCTGTGCCTCATGGCCTTCTCGGTCTTC

ACCATCATCTGCACCATCGGCATCCTGATGTCGGCTCCCAACTTCGTGGAGGCCGTGTCCAAAGACTTTGCGTAACCACG

CCTGGTTCTGTACATGTGGAAAACTCACAGATGGGCAAGGCCTCTGGCTTG
```
Protein:

(SEQ ID NO: 27)
```
MRCSQGGVWLALAASLLHVSLQGEFQRKLYKELVNKYNPLERPVANDSQPLTVYFSLSLLQIMDVDEKNQVLTTNIWLQM

SWTDHYLQWNVSEYPGVKTVRFPDGQIWKPDILLYNSADERFDATFHTNVLVNSSGHCQYLPPGIFKSSCYIDVRWFPFD

VQHCKLKFCSWSYGGWSLDLQMQEADISGYIPSGEWDLVGIPGKRSEKFYECCKEPYPDVTFTVTMRRRTLYYGLNLLIP

CVLISALAL1VFLLPADSGEKISLGITVLTSLTVFMLLVAEIMPATSDSVPLIAQYFASTMIIVGLSVVVTVIVLQYHHH

DPDGGKMPKWTRVILLNWCAWFLRNKRPGEDKVRPACQHKQRRCSLASVEMSAVAPPPASNGNLLYIGFRCLDGMHCAPT

PDSGVVCGRMACSPTHDEHLLHGGQPPEGDPDLAKILEEVRYIANRFRCQDESEAVCSEWKFAACVVDRLCLMAFSVFTI

ICTIGILMSAPNFVEAVSKDFA
```

Example IV a) Ca$^{++}$ Signal Measured by Real Time, High Throughput, Ca Imaging Assays, Using FLIPR: Wild Type Vis L270T (Human)

QM-7 cells were transiently transfected with either wild type or L 270T mutant α7 receptor with Lipofectamine PLUS reagent (Invitrogen), in 175 cm$^2$ flasks. Twenty four hours after the transfection, the cells were collected and re-seeded into a 96-well plate at a density of 40,000 cells/well. Twenty four hours after re-seeding, the cell were incubated with Ca$^{++}$ sensitive dye Fluo 3, washed and stimulated with the selective alpha 7 agonist GTS-21. Cellular Ca$^{++}$ signal was detected with FLIPR, quantified and plotted against the concentration of GTS-21.

As shown in FIG. 1, wild type failed to give a meaningful signal. L270T showed a dose-dependent increase of Ca$^{++}$ signal that saturated at 10 uM GTS-21.

Figure 2:
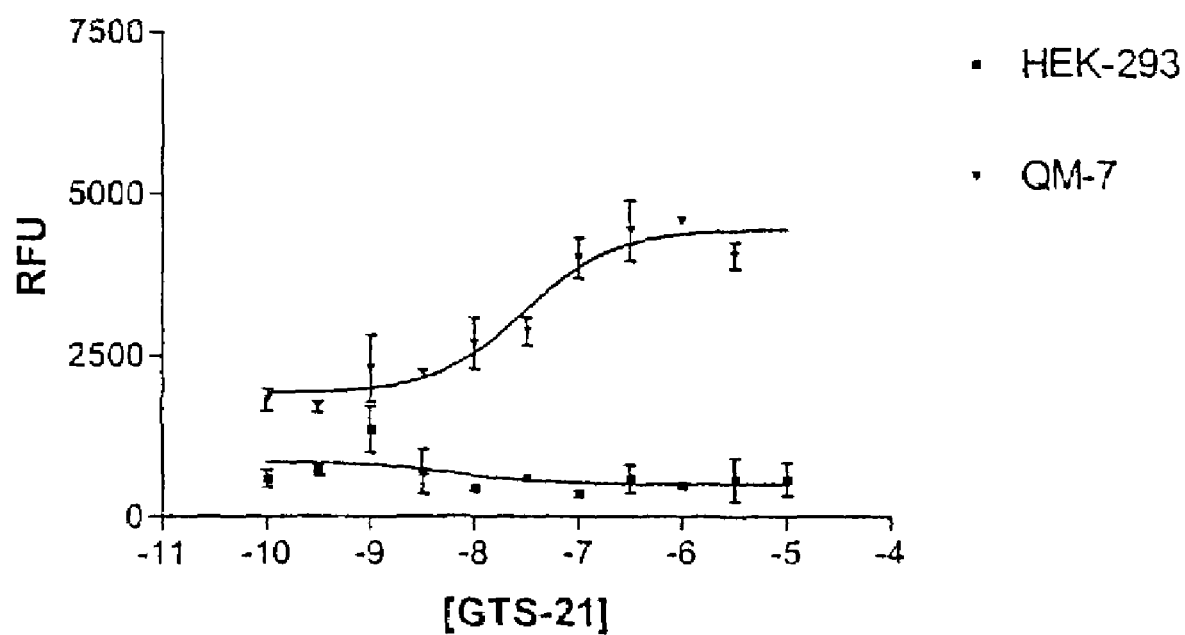
FIG. 2 shows assays, using FLIPR, that compare $Ca^{++}$ signal in QM-7 and HEK-293 cells that are transiently transfected by mutant α7.

QM-7 cells transiently transfected with the mutant are also responsive to acetylcholine, nicotine, epibatidine and the nicotinic alpha 7 specific agonist 4-OH-GTS-21. Signals from epibatidine stimulation can be attenuated by MLA, a nicotinic alpha 7 specific antagonist, in a dose dependent manner. Transient transfection of QM-7 cells offers a fast and simple way to study structure-function relationships of this receptor.

b) Ca$^{++}$ Signal Measured by Real Time, High Throughput, Ca Imaging Assays, Using FLIPR: OM-7 Vis HEK-293 Cells To show the superiority of the QM-7 cell line, either QM-7 cells or HEK-293 cells were transiently transfected with human mutant α7, stimulated with GTS-21, and intracellular Ca$^{++}$ was measured as above. We found that QM-7 cells consistently provided a better signal in this assay (FIG. 2). Similar results were detected when compared with CHO cells.

c) Stable Cell Lines Expressing Human Mutant L270

Figure 3:
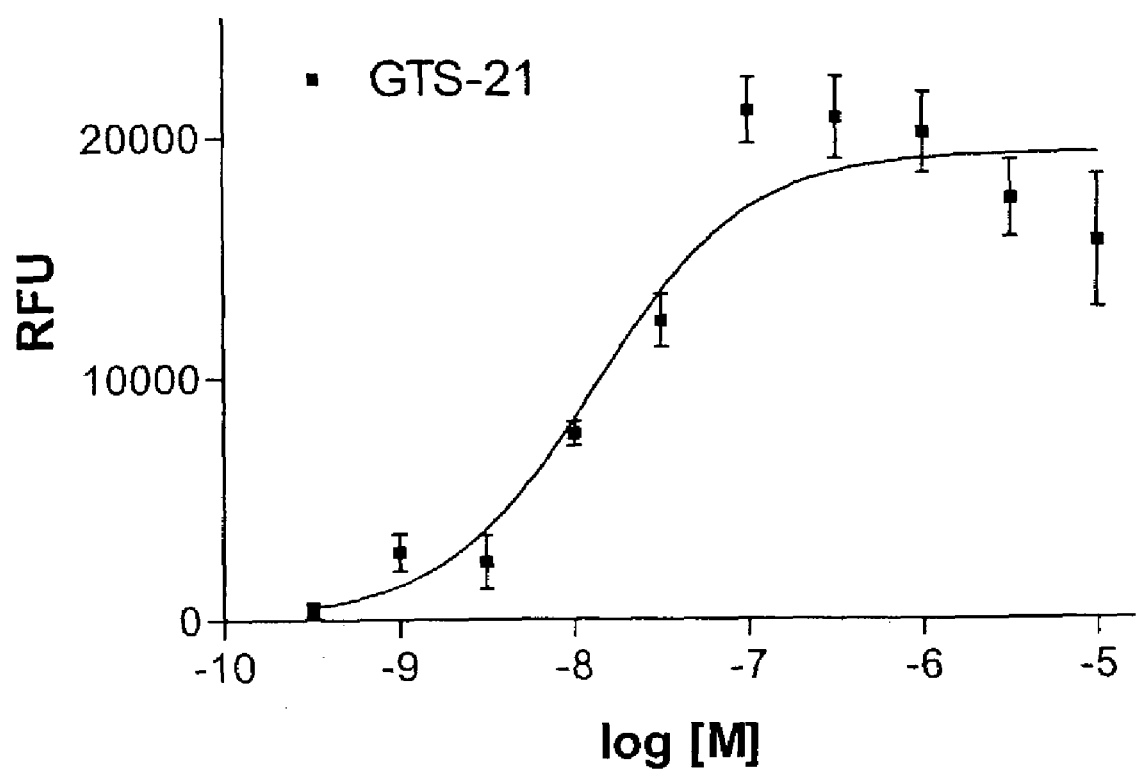
FIG. 3 shows assays, using FLIPR, of a QM-7 cell stably transfected by the human L270T mutant α7.

To obtain stable cell lines expressing human L270T mutant alpha 7, QM-7 cells were transfected with L270T mutant alpha 7 in a neomycin selection vector. Colonies were isolated and assessed as above for functional expression of L270T mutant. A cell line, designated L270T-NIC-19C, was isolated and expanded for use in compound screening. The dose response of GTS-21 in L270T-NIC-19C is shown in FIG. 3.

d) Transient Expressing of Rat and Monkey Mutant L270

Figure 4:
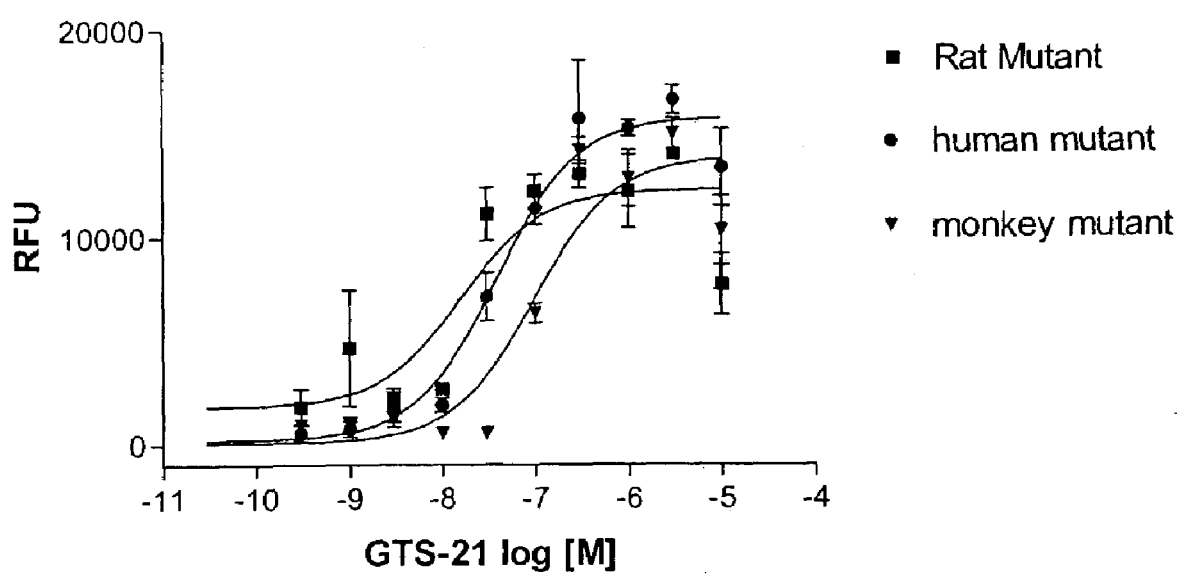
FIG. 4 shows assays, using FLIPR, of a QM-7 cell transiently transfected with human, rat, or monkey L270T mutant nicotinic α7.

The rat and monkey mutant L270T alpha7 were transiently expressed in QM-7 cells along with human mutant L270T. The responses of GTS-21 were tested and the results are shown in FIG. 4.

e) Stable Expression of Monkey Mutant L270

Monkey mutant L270T alpha 7 receptor was stably transfected in a neomycin selection vector. The stable cell line exhibited activity similar to the transient cell line. Rat mutant L270T receptor may be similarly stably transfected.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated in their entirety by reference.

What is claimed is:

1. A QM-7 cell comprising a recombinant mutant nicotinic α7 acetylcholine receptor or a protein subunit thereof.

2. A cell of claim 1, wherein the receptor is a mammalian receptor.

3. A cell of claim 1, wherein the receptor is a human, monkey, or rat receptor.

4. A cell of claim 2, wherein the receptor or the protein subunit has a mutation in the M2 domain.

5. A cell of claim 4, wherein the receptor or the protein subunit is human, monkey, or rat and the Leu at position 270 is substituted with Thr or the Val at position 274 is substituted with Thr.

6. A QM-7 cell comprising a recombinant modified mutant nicotinic α7 acetylcholine receptor protein subunit, in which the ligand binding region is substituted with a ligand binding region for one of a 5HT-3, glycine, $GABA_A$, $GABA_C$, or another nicotinic neuronal receptor.

7. A QM-7 cell comprising a polynucleotide encoding a recombinant mutant nicotinic α7 acetylcholine receptor protein subunit or a fragment.

8. A cell of claim 7, wherein the receptor protein subunit is mammalian.

9. A cell of claim 8, wherein the receptor protein subunit is human, monkey, or rat.

10. A cell of claim 7, wherein the receptor protein subunit has a mutation in the M2 domain.

11. A cell of claim 10, wherein the receptor protein subunit is human, monkey, or rat and the Leu at position 270 is substituted with Thr or the Val at position 274 is substituted with Thr.

12. A QM-7 cell comprising a polynucleotide encoding a recombinant modified mutant nicotinic α7 acetylcholine receptor protein subunit, wherein the ligand binding region of the receptor protein subunit is substituted with a ligand binding region for one of a 5HT-3, glycine, $GABA_A$, $GABA_C$, or another nicotinic neuronal receptor.

13. A method of measuring the activity of a recombinant mutant nicotinic α7 acetylcholine receptor, comprising incubating a QM-7 cell comprising a recombinant mutant nicotinic α7 acetylcholine receptor in the presence of detectable cations, and detecting the presence of the cations in the cell.

14. A method of claim 13, wherein the detectable cations are one of $Ca^{++}$, $Rb^+$, $Na^+$, $K^+$, or $Ba^{++}$.

15. A method of claim 14, wherein the detectable cations are $Ca^{++}$.

16. A method of claim 13, wherein the receptor is a mammalian receptor.

17. A method of claim 16, wherein the receptor is a human, monkey, or rat receptor.

18. A method of one of claims 13, wherein the receptor has a mutation in the M2 domain.

19. A method of one of claims 13, wherein the receptor is human, monkey, or rat and the Leu at position 270 is substituted with Thr or the Val at position 274 is substituted with Thr.

20. A method of identifying an agent which activates a mutant nicotinic α7 acetylcholine receptor, comprising measuring the activity of a QM-7 cell comprising a recombinant mutant nicotinic α7 acetylcholine receptor, exposing the cell to a putative agent and measuring the activity of the receptor in the presence of the agent, and comparing the activity of the receptor in the presence and in the absence of the agent to determine if the agent activates the receptor.

21. A method of claim 20, wherein the agent modulates ion transport through a channel or regulates an allosteric site of the receptor.

22. A method of claim 20, wherein the activity of the receptor is determined by measuring the amount of detectable cation influx into the cell.

23. A method of claim 22, wherein the detectable cation is one of $Ca^{++}$, $Rb^+$, $Na^+$, $K^+$, or $Ba^{++}$.

24. A method of claim 23, wherein the detectable cation is $Ca^{++}$.

25. A method of identifying an agent which inhibits a mutant nicotinic α7 acetylcholine receptor, comprising measuring the activity of a QM-7 cell comprising a recombinant mutant nicotinic α7 acetylcholine receptor in the presence of an agonist of the receptor, measuring the activity of the receptor in the presence of a putative agent and the agonist, and comparing the activity of the receptor in the presence and in the absence of the agent to determine if the agent inhibits the activation of the receptor.

26. A method of claim 25, wherein the agent modulates ion transport through a channel or regulates an allosteric site of the receptor.

27. A method of claim 25, wherein the activity of the receptor is determined by measuring the amount of detectable cation influx into the cell.

28. A method of claim 27, wherein the detectable cation is one of $Ca^{++}$, $Rb^+$, $Na^+$, $K^+$, or $Ba^{++}$.

29. A method of claim 28, wherein the detectable cation is $Ca^{++}$.

30. A method of identifying an agent which modulates the expression of a mutant nicotinic α7 acetylcholine receptor, comprising measuring the amount of a recombinant mutant nicotinic α7 acetylcholine receptor in a QM-7 cell, exposing the cell to a putative agent and measuring the amount of the receptor in the presence of the agent, and comparing the amount of the receptor in the presence and in the absence of the agent to determine if the agent modulates the expression of the receptor.

31. A method of claim 30, wherein the agent modulates the transport of a subunit of the mutant nicotinic α7 acetylcholine receptor to the cell surface membrane.

32. A method of making a QM-7 cell, wherein the cell comprises a recombinant mutant nicotinic α7 acetylcholine receptor or a protein subunit thereof, comprising introducing a construct comprising a nucleic acid encoding a mutant nicotinic α7 actylcholine receptor protein subunit to a QM-7 cell.

33. A method of claim 32, wherein the cell is stably transfected.

34. A method of producing a mutant nicotinic α7 acetylcholine receptor protein subunit, comprising introducing a construct comprising a nucleic acid encoding a mutant nicotinic α7 acetylcholine receptor protein subunit to a QM-7 cell, culturing the cell under conditions effective to express the protein subunit, and recovering the protein subunit.

35. A kit comprising a QM-7 cell, wherein the cell comprises a recombinant mutant nicotinic α7 acetylcholine receptor or a protein subunit thereof, and a $Ca^{++}$ sensitive dye.

* * * * *

SEQUENCE LISTING

<160> NUMBER OF SEQ ID NOS: 27

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 1
gggataacag tcttaacttc tcttaccgtc ttcatgctgc tccgtg        46

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 2
tgaagacggt aagagaagtt aagactgtta tccccaggga aatcttctcc    50

<210> SEQ ID NO 3
<211> LENGTH: 1636
<212> TYPE: DNA
<213> ORGANISM: Homo sapiens

<400> SEQUENCE: 3
gggcgacagc cgagacgtgg agcgcgccgg ctcgctgcag ctccgggact caacatgcgc    60
tgctcgccgg gaggcgtctg gctggcgctg gccgcgtcgc tcctgcacgt gtccctgcaa   120
ggcgagttcc agaggaagct ttacaaggag ctggtcaaga actacaatcc cttggagagg   180
cccgtggcca atgactcgca accactcacc gtctacttct ccctgagcct cctgcagatc   240
atggacgtgg atgagaagaa ccaagttta accaccaaca tttggctgca aatgtcttgg   300
acagatcact atttacagtg gaatgtgtca gaatatccag gggtgaagac tgttcgtttc   360
ccagatggcc agatttggaa accagacatt cttctctata acagtgctga tgagcgcttt   420
gacgccacat tccacactaa cgtgttggtg aattcttctg gcattgcca gtacctgcct   480
ccaggcatat tcaagagttc ctgctacatc gatgtacgct ggtttccctt tgatgtgcag   540
cactgcaaac tgaagtttgg gtcctggtct tacggaggct ggtccttgga tctgcagatg   600
caggaggcag atatcagtgg ctatatcccc aatggagaat gggaccctagt gggaatcccc   660
ggcaagagga gtgaaaggtt ctatgagtgc tgcaaagagc cctacccga tgtcaccttc   720
acagtgacca tgcgccgcag gacgctctac tatggcctca acctgctgat cccctgtgtg   780
ctcatctccg ccctcgccct gctggtgttc ctgcttcctg cagattccgg ggagaagatt   840
tccctgggga taacagtctt aacttctctt accgtcttca tgctgctcgt ggctgagatc   900
atgcccgcaa catccgattc ggtaccattg atagcccagt acttcgccag caccatgatc   960
atcgtgggcc tctcggtggt ggtgacagtg atcgtgctgc agtaccacca ccacgacccc  1020
gacgggggca agatgcccaa gtggaccaga gtcatccttc tgaactggtg cgcgtggttc  1080
ctgcgaatga gaggcccgg ggaggacaag gtgcgcccgg cctgccagca caagcagcgg  1140
cgctgcagcc tggccagtgt ggagatgagc gccgtggcgc cgccgccgc cagcaacggg  1200
aacctgctgt acatcggctt ccgcggcct gacggcgtgc actgtgtccc gaccccgac  1260
tctggggtag tgtgtggccg catggcctgc tcccccacgc acgatgagca cctcctgcac  1320

-continued

```
ggtgggcaac ccccgaggg ggacccggac ttggccaaga tcctggagga ggtccgctac     1380
attgccaacc gcttccgctg ccaggacgaa agcgaggcgg tctgcagcga gtggaagttc     1440
gccgcctgtg tggtggaccg cctgtgcctc atggccttct cggtcttcac catcatctgc     1500
accatcggca tcctgatgtc ggctcccaac ttcgtggagg ctgtgtccaa agactttgcg     1560
taaccacgcc tggttctgta catgtggaaa actcacagat gggcaaggcc tttggcttgg     1620
cgagatttgg gggtgc                                                     1636
```

<210> SEQ ID NO 4
<211> LENGTH: 502
<212> TYPE: PRT
<213> ORGANISM: Homo sapiens

<400> SEQUENCE: 4

```
Met Arg Cys Ser Pro Gly Gly Val Trp Leu Ala Leu Ala Ala Ser Leu
  1               5                  10                  15

Leu His Val Ser Leu Gln Gly Glu Phe Gln Arg Lys Leu Tyr Lys Glu
             20                  25                  30

Leu Val Lys Asn Tyr Asn Pro Leu Glu Arg Pro Val Ala Asn Asp Ser
         35                  40                  45

Gln Pro Leu Thr Val Tyr Phe Ser Leu Ser Leu Leu Gln Ile Met Asp
     50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Thr Ser Leu
            260                 265                 270

Thr Val Phe Met Leu Leu Val Ala Glu Ile Met Pro Ala Thr Ser Asp
        275                 280                 285

Ser Val Pro Leu Ile Ala Gln Tyr Phe Ala Ser Thr Met Ile Ile Val
    290                 295                 300

Gly Leu Ser Val Val Val Thr Val Ile Val Leu Gln Tyr His His His
```

```
            305                 310                 315                 320
Asp Pro Asp Gly Gly Lys Met Pro Lys Trp Thr Arg Val Ile Leu Leu
                325                 330                 335
Asn Trp Cys Ala Trp Phe Leu Arg Met Lys Arg Pro Gly Glu Asp Lys
            340                 345                 350
Val Arg Pro Ala Cys Gln His Lys Gln Arg Arg Cys Ser Leu Ala Ser
        355                 360                 365
Val Glu Met Ser Ala Val Ala Pro Pro Ala Ser Asn Gly Asn Leu
    370                 375                 380
Leu Tyr Ile Gly Phe Arg Gly Leu Asp Gly Val His Cys Val Pro Thr
385                 390                 395                 400
Pro Asp Ser Gly Val Val Cys Gly Arg Met Ala Cys Ser Pro Thr His
                405                 410                 415
Asp Glu His Leu Leu His Gly Gly Gln Pro Pro Glu Gly Asp Pro Asp
            420                 425                 430
Leu Ala Lys Ile Leu Glu Glu Val Arg Tyr Ile Ala Asn Arg Phe Arg
        435                 440                 445
Cys Gln Asp Glu Ser Glu Ala Val Cys Ser Glu Trp Lys Phe Ala Ala
    450                 455                 460
Cys Val Val Asp Arg Leu Cys Leu Met Ala Phe Ser Val Phe Thr Ile
465                 470                 475                 480
Ile Cys Thr Ile Gly Ile Leu Met Ser Ala Pro Asn Phe Val Glu Ala
                485                 490                 495
Val Ser Lys Asp Phe Ala
            500
```

<210> SEQ ID NO 5
<211> LENGTH: 26
<212> TYPE: PRT
<213> ORGANISM: Homo sapiens

<400> SEQUENCE: 5

```
Ser Gly Glu Lys Ile Ser Leu Gly Ile Thr Val Leu Leu Ser Leu Thr
1               5                   10                  15
Val Phe Met Leu Leu Val Ala Glu Ile Met
            20                  25
```

<210> SEQ ID NO 6
<211> LENGTH: 26
<212> TYPE: PRT
<213> ORGANISM: Homo sapiens

<400> SEQUENCE: 6

```
Ser Gly Glu Lys Ile Ser Leu Gly Ile Thr Val Leu Thr Ser Leu Thr
1               5                   10                  15
Val Phe Met Leu Leu Val Ala Glu Ile Met
            20                  25
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 7
ctcttggaat aactgtctta acttctctga ctgtcttcat gc           42

-continued

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 8
gcatgaagac agtcagagaa gttaagacag ttattccaag ag        42

<210> SEQ ID NO 9
<211> LENGTH: 1571
<212> TYPE: DNA
<213> ORGANISM: Rattus sp.

<400> SEQUENCE: 9
ccaccatgtg cggcgggcgg ggaggcatct ggctggctct ggccgcggcg ctgctgcacg    60
tgtccctgca aggcgagttc cagaggaggc tgtacaagga gctggtcaag aactacaacc    120
cgctggagag gccggtggcc aacgactcgc agccgctcac cgtgtacttc tccctgagtc    180
tcctgcagat catggatgtg gatgagaaga accaagtttt aaccaccaac atttggctac    240
aaatgtcttg gacagatcac tatttgcagt ggaacatgtc tgagtacccc ggagtgaaga    300
atgttcgttt tccagatggc cagatttgga accagacat tctcctctat aacagtgctg    360
atgagcgctt tgatgccacg ttccacacca atgttttggt gaatgcatct gggcattgcc    420
agtatctccc tccaggcata ttcaagagct cctgctacat tgacgttcgc tggttccctt    480
ttgatgtgca gcagtgcaaa ctgaagtttg gtcctggtc ctatggaggg tggtcactgg    540
acctgcaaat gcaagaggca gatatcagca gctatatccc caacggagaa tgggatctca    600
tgggaatccc tggcaaaagg aatgagaagt ctctatgagtc ctgcaaagag ccatacccag    660
atgtcaccta cacagtaacc atgcgccgta ggacactcta ctatggcctc aatctgctca    720
tcccttgtgt actcatttca gccctggctc tgctggtatt cttgctgcct gcagactctg    780
gagagaaaat ctctcttgga ataactgtct taacttctct gactgtcttc atgctgcttg    840
tggctgagat catgccagca acatctgatt ctgtgccctt gatagcacaa tacttcgcca    900
gcaccatgat catcgtgggc ctctctgtag tggtgacagt gattgtgctg agatatcacc    960
accatgaccc tgatggtggc aaaatgccta agtggaccag aatcattctc ctgaactggt    1020
gtgcatggtt tctgcgcatg aagaggcccg agaggacaa ggtgcggcca gcttgtcagc    1080
acaagcctcg gcgctgcagc ctggccagtg tggagctgag tgcaggtgct gggccaccca    1140
ccagcaatgg caacctgctc tacattggct tccgaggcct ggagggcatg cactgtgccc    1200
caactccaga ctctggggtc gtatgtggcc gtttggcctg ctccccaaca catgatgagc    1260
acctcatgca cggtgcacac ccctctgatg ggaccccga cctggccaag atcctggagg    1320
aggtccgcta catcgccaac cgcttccgct gccaggacga gagtgaggtg atctgcagtg    1380
aatggaagtt tgcagcctgc gtggtggacc gcttgtgcct catggccttt tcggtctttta    1440
ccatcatctg taccatcggc atcctcatgt cagctccaaa ctttgtggag gctgtgtcca    1500
aagactttgc ttaatgttat caagtaggaa atgcgcagat aagaagagaa tctggagggt    1560
gagaattggg g                                                        1571

<210> SEQ ID NO 10
<211> LENGTH: 502
<212> TYPE: PRT
<213> ORGANISM: Rattus sp.

<400> SEQUENCE: 10

```
Met Cys Gly Gly Arg Gly Gly Ile Trp Leu Ala Leu Ala Ala Leu
 1               5                  10                  15

Leu His Val Ser Leu Gln Gly Glu Phe Gln Arg Arg Leu Tyr Lys Glu
             20                  25                  30

Leu Val Lys Asn Tyr Asn Pro Leu Glu Arg Pro Val Ala Asn Asp Ser
             35                  40                  45

Gln Pro Leu Thr Val Tyr Phe Ser Leu Ser Leu Leu Gln Ile Met Asp
         50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Met Ser Glu Tyr Pro Gly
                 85                  90                  95

Val Lys Asn Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ala Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln Gln Cys Lys Leu Lys Phe Gly Ser Trp Ser Tyr Gly Gly Trp
                165                 170                 175

Ser Leu Asp Leu Gln Met Gln Glu Ala Asp Ile Ser Ser Tyr Ile Pro
            180                 185                 190

Asn Gly Glu Trp Asp Leu Met Gly Ile Pro Gly Lys Arg Asn Glu Lys
            195                 200                 205

Phe Tyr Glu Cys Cys Lys Glu Pro Tyr Pro Asp Val Thr Tyr Thr Val
        210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Thr Ser Leu
            260                 265                 270

Thr Val Phe Met Leu Leu Val Ala Glu Ile Met Pro Ala Thr Ser Asp
            275                 280                 285

Ser Val Pro Leu Ile Ala Gln Tyr Phe Ala Ser Thr Met Ile Ile Val
        290                 295                 300

Gly Leu Ser Val Val Val Thr Val Ile Val Leu Arg Tyr His His His
305                 310                 315                 320

Asp Pro Asp Gly Gly Lys Met Pro Lys Trp Thr Arg Ile Ile Leu Leu
                325                 330                 335

Asn Trp Cys Ala Trp Phe Leu Arg Met Lys Arg Pro Gly Glu Asp Lys
            340                 345                 350

Val Arg Pro Ala Cys Gln His Lys Pro Arg Arg Cys Ser Leu Ala Ser
            355                 360                 365

Val Glu Leu Ser Ala Gly Ala Gly Pro Pro Thr Ser Asn Gly Asn Leu
        370                 375                 380

Leu Tyr Ile Gly Phe Arg Gly Leu Glu Gly Met His Cys Ala Pro Thr
385                 390                 395                 400

Pro Asp Ser Gly Val Val Cys Gly Arg Leu Ala Cys Ser Pro Thr His
                405                 410                 415
```

```
Asp Glu His Leu Met His Gly Ala His Pro Ser Asp Gly Asp Pro Asp
            420                 425                 430

Leu Ala Lys Ile Leu Glu Glu Val Arg Tyr Ile Ala Asn Arg Phe Arg
        435                 440                 445

Cys Gln Asp Glu Ser Glu Val Ile Cys Ser Glu Trp Lys Phe Ala Ala
    450                 455                 460

Cys Val Val Asp Arg Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
                485                 490                 495

Val Ser Lys Asp Phe Ala
            500

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 11
ctcatctcca cgctggccag gtgcag                                           26

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
catgaagagg ccgggagagg ataaggtgcg                                       30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
cgcaccttat cctctcccgg cctcttcatg                                       30

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
ctgcacctgg ccagcgtgga gatgag                                           26

<210> SEQ ID NO 15
<211> LENGTH: 880
<212> TYPE: DNA
<213> ORGANISM: Macaca mulatta

<400> SEQUENCE: 15
ctgcagcctg ccagcgtgga agatgagcgc cgtggcgccg ccgcctgcca gcaacgggaa      60
cctgctgtac atcggcttcc gcggcctgga cggcatgcat tgcgccccga ccccgactc     120
```

-continued

```
cggggtggtg tgcggccgca tggcctgctc ccccacgcac gacgagcacc tcctgcacgg    180
tgggcagccc cccgagggg acccggacct ggccaagatc ctggaggagg tccgctacat    240
cgccaaccgc tttcgctgcc aggacgaaag cgaggcggtc tgcagcgagt ggaagttcgc    300
cgcctgcgtg gtggaccgcc tgtgcctcat ggccttctcg gtcttcacca tcatctgcac    360
catcggcatc ctgatgtcgg ctcccaactt cgtggaggcc gtgtccaaag actttgcgta    420
accacgcctg gttctgtaca tgtggaaaac tcacagatgg gcaaggcctc tggcttggtg    480
agattttggg gtgctaatcc aggacaacat taaacgccac aactccgatg ttcccttctg    540
gctgtcagtc gtgtcgctca cggtttcctc attactttag gtagtaggat ctcagcactc    600
agtttaatac gctcaggtgg gctgatgatc cccttggcac atccgcactg tcggtcagca    660
gggccactga gaagtcattt tgcccattag cccactgcct ggaaagccct tcagagagct    720
cccagtggct cctcaccccg ggacagttgg ttttgcatgt ctgcatgcca cttgccatga    780
aggcctacct gaaaattcaa catttgcttt ttgcttgtgt acaaacctag attgaagcta    840
aaataaacca gactcactaa atccaaaaaa aaaaaaaaa                           880
```

<210> SEQ ID NO 16
<211> LENGTH: 692
<212> TYPE: DNA
<213> ORGANISM: Macaca mulatta

<400> SEQUENCE: 16

```
gtattttgag cgcgtctcga tcagctttcg tttcagtctt ctgtttccgt cacccacacg     60
ggcatattca agagttcctg ctacatcgac gtgcgccggt ttcccttgta tgtgcagcat    120
tgcaaactga gtttggatc ctggtcttat ggaggctggt ccttggatct gcagatgcag    180
gaggcagata tcagtggcta tatccccagt ggagaatggg acctagtggg aattcccggc    240
aagaggagtg aaaagttcta tgagtgctgc aaagagccct accccgatgt caccttcaca    300
gtgaccatgc gccgcaggac cctctactac ggcctcaacc tgctgatccc ctgtgtgctc    360
atctctgccc ttgccctgct ggtgttcctg cttcctgcag attccgggga gaagatttcc    420
ctggggataa cagtcttact ctctctcact gtcttcatgc tgctcgtggc tgagatcatg    480
cccgcaacat ctgattcagt accattgata gcccagtact cgccagcac catgatcatc    540 gtgggcctct ccgtggtggt gacggtgatc gtgctgcagt accaccacca cgaccccgac    600 ggggcaaga tgcccaagtg gaccagagtc atccttctga actggtgcgc gtggttcctg    660
cgcatgaaga ggccgggaga ggataaggtg cg                                  692
```

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 17

```
gaccagcctc cataagacca ggatccaaac ttcag                                35
```

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 18

-continued

```
cgcacgtcga tgtagcagga actcttgaat atgc                               34

<210> SEQ ID NO 19
<211> LENGTH: 494
<212> TYPE: DNA
<213> ORGANISM: Macaca mulatta

<400> SEQUENCE: 19
cattggcggc atctgtcctc cccgacaggg tgcctccagc acttcagatc ccagccgaga    60
gtctggctgc tagcgcccag caaacgtgtc cctgcaaggc gagttccaga ggaagcttta   120
caaggagctg gtcaagaact acaacccctt ggagaggccc gtggccaatg actcgcaacc   180
gctcaccgtc tacttctccc tgagcctcct gcagatcatg gacgcggatg agaagaacca   240
agttttaacc accaacattt ggctgcaaat gtcttggaca gatcactatt tacagtggaa   300
tgtgtcagaa tatccagggg tgaagactgt tcgtttccca gatggccaga tttggaaacc   360
agacattctt ctctataaca gtgcggatga gcgctttgac gccacattcc acaccaacgt   420
gttggtgaat tcttctgggc attgccagta cctgcctcca ggcatattca agagttcctg   480
ctaatcgacg tgcg                                                     494

<210> SEQ ID NO 20
<211> LENGTH: 249
<212> TYPE: DNA
<213> ORGANISM: Macaca mulatta

<400> SEQUENCE: 20
gagaggcggc tctgtggcca caggcgcagg cccgggcgac agccgatacg tgaggcgcgc    60
cggcccgcgg cagctccggg actcaacatg cgctgctcgc agggaggcgt ctggctggct   120
ctggccgcgt cgctcctgca tgtgtccctg caaggcgagt tccagaggaa gctttacaag   180
gagctggtca agaactacaa ccccttggag aggcccgtgg ccaatgactc gcaaccgctc   240
accgtctac                                                          249

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 21
ctcaacatgc gctgctcgca gggagg                                        26

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 22
ccaagccaga ggccttgccc atctgtgag                                     29

<210> SEQ ID NO 23
<211> LENGTH: 1571
<212> TYPE: DNA
<213> ORGANISM: Macaca mulatta

<400> SEQUENCE: 23
```

-continued

```
ctcaacatgc gctgctcgca gggaggcgtc tggctggctc tggccgcgtc gctcctgcat      60
gtgtccctgc aaggcgagtt ccagaggaag ctttacaagg agctggtcaa gaactacaac     120
cccttggaga ggcccgtggc caatgactcg caaccgctca ccgtctactt ctccctgagc     180
ctcctgcaga tcatggacgt ggatgagaag aaccaagttt taaccaccaa catttggctg     240
caaatgtctt ggacagatca ctatttacag tggaatgtgt cagaatatcc aggggtgaag     300
actgttcgtt tcccagatgg ccagatttgg aaaccagaca ttcttctcta taacagtgcg     360
gatgagcgct ttgacgccac attccacacc aacgtgttgg tgaattcttc tgggcattgc     420
cagtacctgc ctccaggcat attcaagagt tcctgctaca tcgacgtgcg ctggtttccc     480
tttgatgtgc agcattgcaa actgaagttt ggatcctggt cttatggagg ctggtccttg     540
gatctgcaga tgcaggaggc agatatcagt ggctatatcc ccagtggaga atgggaccta     600
gtgggaattc ccggcaagag gagtgaaaag ttctatgagt gctgcaaaga gccctacccc     660
gatgtcacct tcacagtgac catgcgccgc aggaccctct actacggcct caacctgctg     720
atcccctgtg tgctcatctc tgcccttgcc ctgctggtgt tcctgcttcc tgcagattcc     780
ggggagaaga tttccctggg gataacagtc ttactctctc tcactgtctt catgctgctc     840
gtggctgaga tcatgcccgc aacatctgat tcagtaccat tgatagccca gtacttcgcc     900
agcaccatga tcatcgtggg cctctcggtg gtggtgacgg tgatcgtgct gcagtaccac     960
caccacgacc ccgacggggg caagatgccc aagtggacca gagtcatcct tctgaactgg    1020
tgcgcgtggt tcctgcgcat gaagaggccc ggagaggata aggtgcgccc ggcctgccag    1080
cacaagcagc gccgctgcag cctggccagc gtggagatga gcgccgtggc cgccgcgcct    1140
gccagcaacg ggaacctgct gtacatcggc ttccgcggcc tggacggcat gcattgcgcc    1200
ccgaccccca actccggggt ggtgtgcggc cgcatggcct gctcccccac gcacgacgag    1260
cacctcctgc acggtgggca gccccccgag gggacccgg acctggccaa gatcctggag    1320
gaggtccgct acatcgccaa ccgctttcgc tgccaggacg aaagcgaggc ggtctgcagc    1380
gagtggaagt cgccgcctg cgtggtggac cgcctgtgcc tcatggcctt ctcggtcttc    1440
accatcatct gcaccatcgg catcctgatg tcggctccca acttcgtgga ggccgtgtcc    1500
aaagactttg cgtaaccacg cctggttctg tacatgtgga aaactcacag atgggcaagg    1560
cctctggctt g                                                         1571
```

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 24
gggataacag tcttaacttc tctcactgtc ttc      33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 25
gaagacagtg agagaagtta agactgttat ccc      33

<210> SEQ ID NO 26
<211> LENGTH: 1571
<212> TYPE: DNA
<213> ORGANISM: Macaca mulatta

<400> SEQUENCE: 26

```
ctcaacatgc gctgctcgca gggaggcgtc tggctggctc tggccgcgtc gctcctgcat      60
gtgtccctgc aaggcgagtt ccagaggaag ctttacaagg agctggtcaa gaactacaac     120
cccttggaga ggcccgtggc caatgactcg caaccgctca ccgtctactt ctccctgagc     180
ctcctgcaga tcatggacgt ggatgagaag aaccaagttt taaccaccaa catttggctg     240
caaatgtctt ggacagatca ctatttacag tggaatgtgt cagaatatcc aggggtgaag     300
actgttcgtt tcccagatgg ccagatttgg aaaccagaca ttcttctcta taacagtgcg     360
gatgagcgct ttgacgccac attccacacc aacgtgttgg tgaattcttc tgggcattgc     420
cagtacctgc ctccaggcat attcaagagt tcctgctaca tcgacgtgcg ctggtttccc     480
tttgatgtgc agcattgcaa actgaagttt ggatcctggt cttatggagg ctggtccttg     540
gatctgcaga tgcaggaggc agatatcagt ggctatatcc cagtggagaa atgggaccta     600
gtgggaattc ccggcaagag gagtgaaaag ttctatgagt gctgcaaaga gccctacccc     660
gatgtcacct tcacagtgac catgcgccgc aggaccctct actacggcct caacctgctg     720
atccctgtg tgctcatctc tgcccttgcc ctgctggtgt tcctgcttcc tgcagattcc     780
ggggagaaga tttccctggg gataacagtc ttaacttctc tcactgtctt catgctgctc     840
gtggctgaga tcatgcccgc aacatctgat tcagtaccat tgatagccca gtacttcgcc     900
agcaccatga tcatcgtggg cctctcggtg gtggtgacgg tgatcgtgct gcagtaccac     960
caccacgacc ccgacggggg caagatgccc aagtggacca gagtcatcct tctgaactgg    1020
tgcgcgtggt tcctgcgcat gaagaggccc ggagaggata aggtgcgccc ggcctgccag    1080
cacaagcagc gccgctgcag cctggccagc gtggagatga cgccgtggc cgccgcgcct    1140
gccagcaacg ggaacctgct gtacatcggc ttccgcggcc tggacggcat gcattgcgcc    1200
ccgaccccg actccggggt ggtgtgcggc cgcatggcct gctccccac gcacgacgag    1260
cacctcctgc acggtgggca gccccccgag ggggacccgg acctggccaa gatcctggag    1320
gaggtccgct acatcgccaa ccgctttcgc tgccaggacg aaagcgaggc ggtctgcagc    1380
gagtggaagt cgccgcctg cgtggtggac cgcctgtgcc tcatggcctt ctcggtcttc    1440
accatcatct gcaccatcgg catcctgatg tcggctccca acttcgtgga ggccgtgtcc    1500
aaagactttg cgtaaccacg cctggttctg tacatgtgga aaactcacag atgggcaagg    1560
cctctggctt g                                                         1571
```

<210> SEQ ID NO 27
<211> LENGTH: 502
<212> TYPE: PRT
<213> ORGANISM: Macaca mulatta

<400> SEQUENCE: 27

Met Arg Cys Ser Gln Gly Gly Val Trp Leu Ala Leu Ala Ala Ser Leu
 1               5                  10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp

```
            50                  55                  60
Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Ser Gly Glu Trp Asp Leu Val Gly Ile Pro Gly Lys Arg Ser Glu Lys
            195                 200                 205

Phe Tyr Glu Cys Cys Lys Glu Pro Tyr Pro Asp Val Thr Phe Thr Val
            210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Thr Ser Leu
            260                 265                 270

Thr Val Phe Met Leu Leu Val Ala Glu Ile Met Pro Ala Thr Ser Asp
            275                 280                 285

Ser Val Pro Leu Ile Ala Gln Tyr Phe Ala Ser Thr Met Ile Ile Val
            290                 295                 300

Gly Leu Ser Val Val Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335

Asn Trp Cys Ala Trp Phe Leu Arg Met Lys Arg Pro Gly Glu Asp Lys
                340                 345                 350

Val Arg Pro Ala Cys Gln His Lys Gln Arg Arg Cys Ser Leu Ala Ser
            355                 360                 365

Val Glu Met Ser Ala Val Ala Pro Pro Ala Ser Asn Gly Asn Leu
            370                 375                 380

Leu Tyr Ile Gly Phe Arg Gly Leu Asp Gly Met His Cys Ala Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
                420                 425                 430

Leu Ala Lys Ile Leu Glu Glu Val Arg Tyr Ile Ala Asn Arg Phe Arg
            435                 440                 445

Cys Gln Asp Glu Ser Glu Ala Val Cys Ser Glu Trp Lys Phe Ala Ala
            450                 455                 460

Cys Val Val Asp Arg Leu Cys Leu Met Ala Phe Ser Val Phe Thr Ile
465                 470                 475                 480
```

```
Ile Cys Thr Ile Gly Ile Leu Met Ser Ala Pro Asn Phe Val Glu Ala
                485                 490                 495
Val Ser Lys Asp Phe Ala
            500
```